US008623606B2

(12) United States Patent
Hausch et al.

(10) Patent No.: US 8,623,606 B2
(45) Date of Patent: Jan. 7, 2014

(54) SCREENING METHOD FOR GPCR LIGANDS

(75) Inventors: Felix Hausch, München (DE); Francisco Perez-Balderas, Oxford (GB)

(73) Assignee: Max-Planck-Gesellschaft zur Forderung der wissenschaften E.V., Munich (DE)

( * ) Notice: Subject to any disclaimer, the term of this patent is extended or adjusted under 35 U.S.C. 154(b) by 642 days.

(21) Appl. No.: 12/310,296

(22) PCT Filed: Aug. 9, 2007

(86) PCT No.: PCT/EP2007/007071
§ 371 (c)(1), (2), (4) Date: Jul. 7, 2009

(87) PCT Pub. No.: WO2008/022716
PCT Pub. Date: Feb. 28, 2008

(65) Prior Publication Data
US 2009/0286259 A1 Nov. 19, 2009

Related U.S. Application Data

(60) Provisional application No. 60/839,170, filed on Aug. 22, 2006.

(51) Int. Cl.
*G01N 33/53* (2006.01)
*C07K 14/705* (2006.01)

(52) U.S. Cl.
USPC .......................................... 435/7.1; 530/350

(58) Field of Classification Search
None
See application file for complete search history.

(56) References Cited

U.S. PATENT DOCUMENTS

| | | | |
|---|---|---|---|
| 5,367,058 A | 11/1994 | Pitner et al. | |
| 6,335,155 B1 | 1/2002 | Wells et al. | |
| 6,713,651 B1 * | 3/2004 | Moran et al. | 564/372 |
| 2001/0051348 A1 | 12/2001 | Lee | |
| 2002/0155505 A1 | 10/2002 | Wells et al. | |
| 2003/0232391 A1 | 12/2003 | Prescott et al. | |
| 2006/0147987 A1 | 7/2006 | Gold | |

FOREIGN PATENT DOCUMENTS

| | | |
|---|---|---|
| EP | 1 094 072 A1 | 4/2001 |
| WO | WO 01/29086 A1 | 4/2001 |

OTHER PUBLICATIONS

Gronemeyer et al., "Adding value to fusion proteins through covalent labelling," Current Opinion in Biotechnology, 16: 453-458 (2005).
Muralidharan, et al., "Protein ligation: an enabling technology for the biophysical analysis of proteins," Nature Methods, 3(6): 429-438 (2006).
Hoare et al., "Conformational states of the corticotropin releasing factor 1 (CFR$_1$) receptor: detection, and pharmacological evaluation by peptide ligands," Peptides, 24: 1881-1897 (2003).
Dean et al., "Mechanisms of Ligand Binding to the Parathyroid Hormone (PTH)/PTH-Related Protein Receptor: Selectivity of a Modified PTH(1-15) Radioligand for Ga$_s$-Coupled Receptor Conformations," Molecular Endocrinology, 20(4): 931-943 (2006).
Fletcher, et al., "Protein surface recognition and proteomimetics: mimics of protein surface structure and function," Curr. Opin. Chem. Biol., 9(6): 632-638 (2005).
Hoare et al., "Mechanism of Corticotropin-Releasing Factor Type I Receptor Regulation by Nonpeptide Antagonists," Molecular Pharmacology, 63(3): 751-765 (2003).
Zhang et al., "Pharmacological Characterization of a Novel Nonpeptide Antagonist Radioligand, (±)-N[2-Methyl-4-methoxyphenyl]-1-(1-(methoxymenthyl) propyl)-6-methyl-1-H-1,2,3-triazolo[4,5-c]pyridin-4-amine ([$^3$H]SN003) for Corticotropin-Releasing Factor$_1$ Receptors," The Journal of Pharmacology and Experimental Therapeutics, 305: 57-69 (2003).
Thomsen et al., "Functional assays for screening GPCR targets," Curr Opin Biotechnol., 16(6): 655-665 (2005).
Greasley, et al., "G-protein-coupled receptor screening technologies," Drug Discovery Today: Technologies, 2(2): 163-170 (2005).
Milligan, "High-content assays for ligand regulation of G-protein coupled receptors," Drug Discovery Today, 8(13): 579-585 (2003).
Williams, "cAMP detection methods in HTS: selecting the best from the rest," Nat Rev Drug Discov., 3: 125-135 (2004).
Hoffmann, et al., "A FlAsH-based FRET approach to determine G protein coupled receptor activation in living cells," Nat Methods, 2(3): 171-176 (2005).
Gales, et al., "Real-time monitoring of receptor and G-protein interactions in living cells," Nat Methods, 2(3): 177-184 (2005).
Connolly, "Chemical synthesis of oligonucelotides containing a free sulphydryl group and subsequent attachment of thiol specific probes," Nucleic Acids Research, 13(12): 4485-4502 (1985).
Sproat, et al., "The synthesis of protected 5' -mercapto-2',5'-dideoxyribonucleoside-3'-O-phosphoramidites; uses of 5'-mercapto-oligodeoxyribonucleotides," Nucleic Acids Research, 15(12): 4837-4848 (1987).
Zuckermann, et al., "Efficient methods for attachment of thiol specific probes to the 3'-ends of synthetic oligodeoxyribonucleotides," Nucleic Acids Research, 15(13): 5305-5321 (1987).
Li, et al., "Enzyme-linked synthetic oligonucleotide probes: non-radioactive detection of enterotoxigenic *Escherichia coli* in faecal speciments," Nucleic Acids Research, 15(13): 5275-5287 (1987).
Dreyer, et al., "Sequence-specific cleavage of single-stranded DNA: Oligodeoxynucleotide-EDTA-Fe(II)," Biochemistry, 82: 968-972 (1985).
Connolly, "The synthesis of oligonucleotides containing a primary amino group at the 5'-terminus," Nucleic Acids Research, 15(7): 3131-3139 (1987).

(Continued)

*Primary Examiner* — Ruixiang Li
(74) *Attorney, Agent, or Firm* — Maryellen Feehery Hank; Reed Smith LLP

(57) ABSTRACT

This invention relates to a method of identifying a compound capable of binding to a target domain of a G-protein coupled receptor comprising the steps of: (a) providing a receptor comprising said target domain and a first group linked to said target domain; (b) bringing into contact said receptor of (a) with a test molecule comprising a second group and said compound linked to each other, wherein said first group binds said second group; and (c) determining, subsequent to the binding of said first group to said second group, whether said compound binds to said target domain.

8 Claims, 5 Drawing Sheets

(56) References Cited

OTHER PUBLICATIONS

Figure 2:
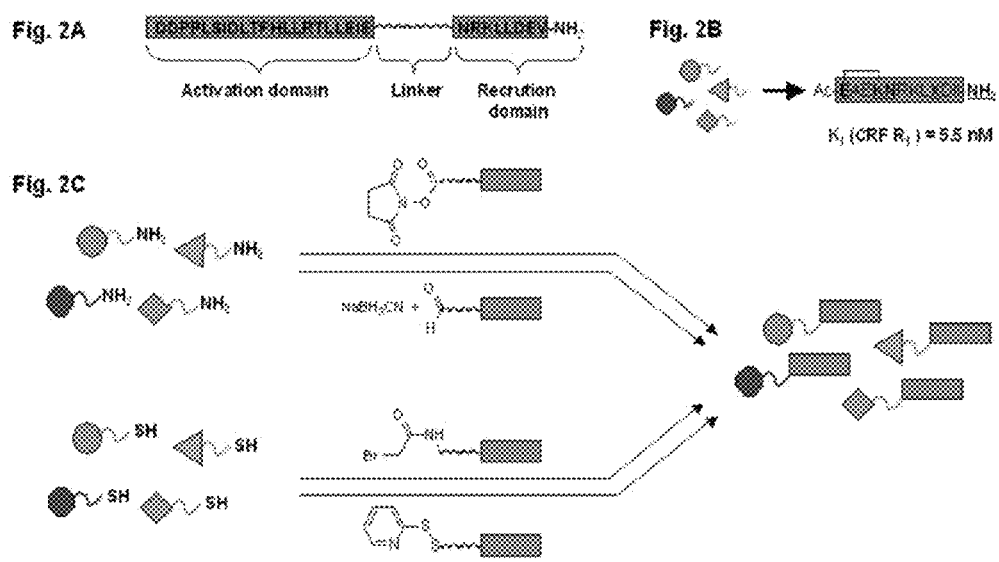

Sinha, et al., "The preparation and application of functionalised synthetic oligonucleotides: III. Use of H-phosphonate derivatives of protected amino-hexanol and mercapto-propanol or-hexanol," Nucleic Acids Research, 16(6): 2659-2669 (1988).

Kumar, et al., "A simple method for introducing a thio group at the 5'-end of synthetic oligonucleotides," Nucleic Acids Research, 19(16): 4561 (1991).

Gupta, et al., "A Universal Solid Support for the Synthesis of 3'-Thiol Group Containing Oligonucleotides," Tetrahedron Letters, 31(17): 2471-2474 (1990).

Asseline, et al., "Solid-Phase Preparation of 5', 3'-Heterobifunctional Oligodeboxyribonucleotides Using Modified Solid Supports," Tetrahedron, 48(7): 1233-1254 (1992).

Durand, et al., "Circular dichroism studies of an oligodeoxyribonucleotide containing a hairpin loop made of a hexaethylene glycol chain: conformation and stability," Nucleic Acids Research, 18(21): 6353-6359, 1990.

Salunkhe, et al., "Control of Folding and Binding of Oligonucleotides by Use of a Nonnucleotide Linker," J. Am. Chem. Soc., 114: 8768-8772 (1992).

Dolinnaya, et al., "Oligonucleotide circularization by template-directed chemical ligation," Nucleic Acids Research, 21(23): 5403-5407 (1993).

Takeshita, et al., "Oligodeoxynucleotides Containing Synthetic Abasic Sites," The Journal of Biological Chemistry, 262(21): 10171-10179 (1987).

Kalnik, et al., "NMR Studies of Abasic Sites in DNA Duplexes: Deoxyadenasine Stacks into the Helix Opposite the Cyclic Analogue of 2-Deoxyribose," Biochemistry, 27: 924-931 (1988).

Zendegui, et al., "In vivo stability and kinetics of absorption and disposition of 3' phosphopropyl amine oligonucleotides," Nucleic Acids Research, 20(2): 307-314 (1992).

Yoo, et al., "Synthesis of Oligonucleotides Containing 3'-Alkyl Carboxylic Acids Using Universal, Photolabile Solid Phase Synthesis Supports," J. Org. Chem, 60: 3358-3364 (1995).

Venkatesan, et al., "Improved Utility of Photolabile Solid Phase Synthesis Supports for the Synthesis of Oligonucelotides Containing 3'-Hydroxyl Termini," J. Org. Chem., 61: 525-529 (1996).

McMinn, et al., "Novel Solid Phase Synthesis Supports for the Preparation of Oligonucleotides Containing 3'-Alkyl Amines," Tetrahedron, 52(11): 3827-3840 (1996).

Owens, et al., "Identification of two short internal ribosome entry sites selected from libraries of random oligonucelotides," PNAS, 98(4): 1471-1476 (2001).

Ghahroudi, et al., "Selection and identification of single domain antibody fragments from camel heavy-chain antibodies," FEBS Letters, 414: 521-526 (1997).

Murphy, et al., "Matrix metalloproteinase degradation of elastin, type IV collagen and proteoglycan," Biochem. J., 277: 277-279 (1991).

Bebbington, et al., "High-Level Expression of a Recombinant Antibody from Myeloma Cells Using a Glutamine Synthetase Gene as an Amplifiable Selectable Marker," Bio/Technology, 10: 169-175 (1992).

Kolb, et al., "Click Chemistry: Diverse Chemical Function from a Few Good Reactions," Angew. Chem. Int. Ed., 40: 2004-2021 (2001).

Kolb et al., "The growing impact of click chemistry on drug discovery," Drug Discovery Today, 8(24): 1128-1137 (2003).

Tornoe, et al., "Peptidotriazoles on Solid Phase: [1,2,3]-Triazoles by Regiospecific Copper(I)-Catalyzed 1,3-Dipolar Cycloadditions of Terminal Alkynes to Azides," J. Org. Chem., 67: 3057-3064 (2002).

Rostovtsev, et al., "A Stepwise Huisgen Cycloaddition Process: Copper(I)-Catalyzed Regioselective "Ligation" of Azides and Terminal Alkynes," Agnew. Chem. Int. Ed., 41(14): 2596-2599 (2002).

Perez-Balderas, et al., "Multivalent Neoglycoconjugates by Regiospecific Cycloaddition of Alkynes and Azides Using Organic-Soluble Copper Catalysts," Organic Letters, 5(11): 1951-1954 (2003).

Lin et al., "A Chemoenzymatic Approach to Glycopeptide Antibotics," J. Am. Chem. Soc., 126: 13998-14003 (2004).

Lundquist, et al., "Improved solid-phase peptide synthesis method utilizing α-azide-protected amino acids," Org. Lett., 3(5): 781-783 (2001).

Kohn, et al., "The Staudinger Ligation—A Gift to Chemical Biology," Angew. Chem. Int. Ed., 43: 3106-3116 (2004).

Wu, et al., "Building Complex Glycopeptides: Development of a Cysteine-Free Native Chemical Ligation Protocol," Angew. Chem. Int. Ed., 45: 4116-4125 (2006).

Carrillo, et al., "Iterative, Aqueous Synthesis of $\beta^3$-Oligopeptides without Coupling Reagents," J. Am. Chem. Soc., 128: 1452-1453 (2006).

Rivier, et al., "Characterization of rat hypothalamic corticotropin-releasing factor," Proc. Natl. Acad. Sci. USA, 80: 4851-4855 (1983).

Morris, et al., "Isolation and characterization of human calcitonin gene-related peptide," Nature, 308: 746-748 (1984).

Steenbergh, et al., "A second human calcitonin/CGRP gene," FEBS Letters, 183(2): 403-407 (1985).

Cooper, et al., "Purification and characterization of a peptide from amyloid-rich pancreases of type 2 diabetic patients," Proc. Natl. Acad. Sci. USA, 84: 8628-8632 (1987).

Neher, et al., "Menschliches Calcitonin. III. Struktur von Calcitonin M and $D^1$," Helvetica Chimica Acta, 51: 1900-1905 (1968).

Kitamura, et al., "Adrenomedullin: A Novel Hypotensive Peptide Isolated From Human Pheochromocytoma," Biochemical and Biophysical Research Communications, 192(2): 553-560 (1993).

Rist et al., "From Micromolar to Nanomolar Affinity: A Systematic Approach to Identify the Binding Site of CGRP at the Human Calcitonin Gene-Related Peptide 1 Receptor," J. Med. Chem., 41: 117-123 (1998).

Rivier et al., "Characterization of rat hypothalamic corticotropin-releasing factor," Proc. Natl. Acad. Sci. USA, 80: 4851-4855 (1983).

Yamada, et al., "New Class of Corticotropin Releasing Factor (CFR) Antagonist: Small Peptides Having High Binding Affinity for CRF Receptor," Journal of Medicinal Chemistry, 47(5): 1075-1078 (2004).

Keutmann, et al., "Complete Amino Acid Sequence of Human Parathyroid Hormone," Biochemistry, 17(26): 5723-5729 (1978).

Brewer, et al., "Human Parathyroid Hormone: Amino-Acid Sequence of the Amino-Terminal Residues 1-34," Proc. Nat. Acad. Sci. USA, 69(12): 3585-3588 (1972).

Usdin, et al., "TIP39: a new neuropeptide and PTH2-receptor agonist from hypothalamus," Nature Neuroscience, 2(11): 941-943 (1999).

Nutt, et al., "Removal of Partial Agonish From Parathyroid Hormons (PTH)-Related Protein-(7-34)$NH_2$ by Substitution of PTH Amino Acids at Positions 10 and 11," Endocrinology, 127(1): 491-493, 1990.

Carter, et al., "Studies of the N-Terminal Region of a Parathyroid Hormone-Related Peptide(1-36) Analog: Receptor Subtype-Selective Agonists, Antagonists, and Photochemical Cross-Linking Agents," Endocrinology, 140(11): 4972-4981 (1999).

Whitmore, et al., "Human secretin (SCT): gene structure, chromosome location, and distribution of mRNA," Cytogenetics and Cell Genetics, 90: 47-52 (2000).

Thomsen, et al., "The Amino Acid Sequence of Human Glucagon," FEBS Letters, 21(3): 315-319 (1972).

Mayo, et al., "International Union of Pharmacology. XXXV. The Glucagon Receptor Family," Pharmacological Reviews, 55(1): 167-194 (2003).

Hernandez, et al., "Synthesis and Relative Potencies of New Constrained CFR Antagonist," J. Med. Chem., 36: 2860-2867 (1993).

Miranda, et al., "Conformationally Restricted Competitive Antagonists of Human/Rat Corticotropin-Releasing Factor," J. Med. Chem., 37: 1450-1459 (1994).

Gulyas, et al., "Potent structurally constrained agonists and competitive antagonists of corticotropin-releasing factor," Proc. Nat. Acad. Sci. USA, 92: 10575-10579 (1995).

Miranda, et al., "Constrained corticotropin-releasing factor antagonists with i-(i+3) Glu-Lys bridges," J. Med. Chem. 40(22): 3651-3658 (1997).

Rivier, et al., "Minimal-size, constrained corticotropin-releasing factor agonists with i-(i+3) Glu-Lys and Lys-Glu bridges," J. Med. Chem., 41(14): 2614-2620 (1998).

(56) References Cited

OTHER PUBLICATIONS

Rivier, et al., "Astressin analogues (corticotropin-releasing factor antagonists) with extended duration of action in the rat," J. Med. Chem., 41(25): 5012-5019 (1998).

Rivier et al., "Constrained corticotropin releasing factor antagonists (astressing analogues) with long duration of action in the rat," J. Med. Chem., 42(16): 3175-3182 (1999).

Rivier, et al., "Potent and long-acting corticotropin releasing factor (CRF) receptor 2 selective peptide competitive antagonists," J. Med. Chem., 45(21): 4737-4747 (2002).

Rijkers, et al., "Structure-activity studies on the corticotropin-releasing factor antagonist astressin, leading to a minimal sequence necessary for antagonistic activity," Chembichem, 5(3): 340-348 (2004).

Rijkers, et al., "An optimized solid phase synthesis strategy—including on-resin lactamization-of astressin, its retro-, inverso-, and retro-inverso-isomers as corticotropin-releasing factor antagonists," Biopolymers, 63(2): 141-149 (2002).

Rijkers, et al., "Synthesis and biological activity of N-terminal lipidated and/or fluorescently labeled conjugates of astressin as cortiocotropin-releasing factor antagonists," Bioorg Med Chem, 12(19): 5099-5106 (2004).

Lebeau, et al., "Synthesis of New Phospholipids Linked to Steroid-Hormone Derivatives Designed for Two-Dimensional Crystallization of Protein," Helvetica Chimica Acta, 74: 1697-1706 (1991).

Rensen, et al., "Design and Synthesis of Novel N-Acetylgalactosamine-Terminated Glycolipids for Targeting of Lipoproteins to the Hepatic Asialoglycoprotien Receptor," J. Med. Chem., 47: 5798-5808 (2004).

Reverberi et al., "Factors affecting the antigen-antibody reaction" Blood Transfus. Nov. 2007; 5(4):227-40.

Definition of "hydrogen bond" http://www.thefreedictionary.com/hydrogen+bond, 2003.

Definition of "van der Waals force" http://www.thefreedictionary.com/van+der+Waals+force, 2005.

"Chemical bond" http://en.wikipedia.org/wiki/Chemcial_bond, pp. 1-13, Feb. 25, 2013.

Living Science Chemistry for Class 10, Raymond Fernandes, Chapter 20, Chemical Bonding, Ratna Sagar P. Ltd., 2008.

* cited by examiner

Figure 1
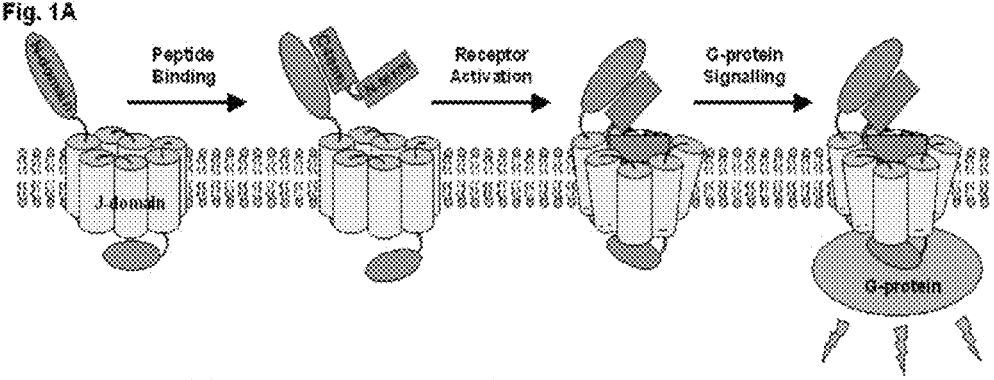
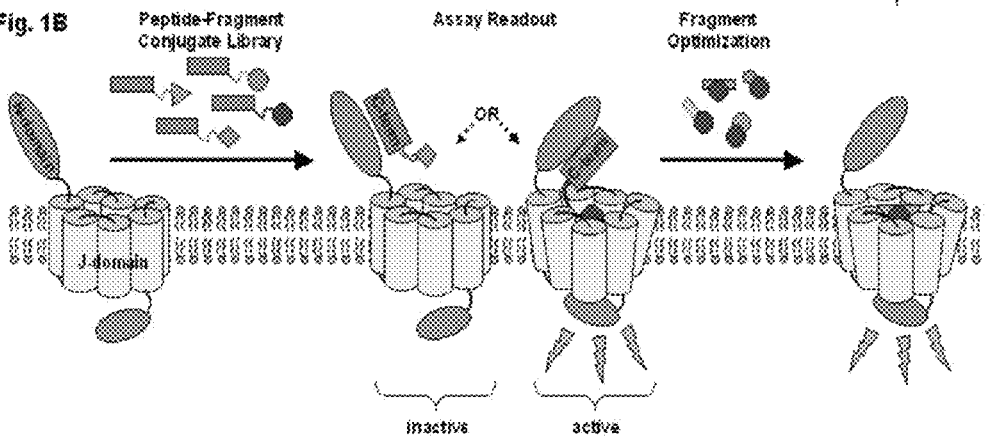

SCREENING METHOD FOR GPCR LIGANDS

This application is the United States National Stage of International Application No. PCT/EP2007/007071, filed Aug. 9, 2007, which was published as International Publication No. WO 2008/022716 A2 and WO 2008/022716 A3, and which claims the benefit of U.S. Provisional Application No. 60/839,170 filed Aug. 22, 2006, and the text of applications 60/839,170 and PCT/EP2007/007071 is incorporated by reference in its entirety herewith.

SEQUENCE LISTING

The instant application contains a Sequence Listing which has been submitted in ASCII format via EFS-Web and is hereby incorporated by reference in its entirety. Said ASCII copy, created on Jul. 15, 2013, is named 09-40041-US (883153.20008)_SL.txt and is 11,920 bytes in size.

This invention relates to a method of identifying a compound capable of binding to a target domain of a G-protein coupled receptor comprising the steps of: (a) providing a receptor comprising said target domain and a first group linked to said target domain; (b) bringing into contact said receptor of (a) with a test molecule comprising a second group and said compound linked to each other, wherein said first group binds said second group; and (c) determining, subsequent to the binding of said first group to said second group, whether said compound binds to said target domain.

In this specification, a number of documents including patent applications and manufacturer's manuals is cited. The disclosure of these documents, while not considered relevant for the patentability of this invention, is herewith incorporated by reference in its entirety.

G-Protein Coupled Receptors (GPCR) comprise several important drug targets that are implicated in severe human diseases. In case of the secretin family (subfamily B1) of G-Protein Coupled Receptors (GPCR) these diseases include osteoporosis, type II diabetes and depression[1,2]. Despite considerable efforts, however, numerous drug discovery programs have been unsuccessful to deliver clinically useful small molecules for the peptidergic class B1 GPCRs so far[1,3].

Fragments are defined as chemical moieties with a molecular weight of 200-250 Da that can be part of a larger drug-like molecule. They have been proposed as a more systematic alternative to the classical screening procedure[4-6]: (i) Due to their small size, fragments provide a better coverage of the respective chemical space[7]; (ii) fragments have a higher probability to fit into a given binding pocket[8]; and (iii) fragments are likely to have a better binding energy/heavy atom ratio (ligand efficiency)[9] thus making them better starting points for a drug development process.

The major drawback of fragments is their weak initial affinity which usually is below the detection limit of typical high-throughput screening assays.

U.S. Pat. No. 6,335,155 (Sunesis Pharmaceuticals, Inc.) describes methods for rapidly identifying small organic molecule ligands for binding to biological target molecules. The target molecule has to contain a thiol group adjacent to the binding site of interest. This thiol group, if not present, has to be introduced. The compounds to be screened for their capability to bind to the site of interest on the target molecule also comprises a thiol group. In case binding of a compound to the site of interest occurs, a disulfide bond will be formed. As such, the method allows to capture—and subsequently detect by means of mass spectrometry—binding molecules. In case no binding occurs, no disulfide is formed. An increase of the local concentration of potentially binding compounds prior to binding to the site of interest does not occur. In other words, binding at the site of interest has to take place in a first step in order to permit formation of the disulfide bond.

In view of the limitations of the methods described in the prior art, the technical problem underlying the present invention was therefore the provision of means and methods for the identification of potentially pharmaceutically relevant compounds.

Accordingly, this invention relates to a method of identifying a compound capable of binding to a target domain of a G-protein coupled receptor comprising the steps of: (a) providing a receptor comprising said target domain and a first group linked to said target domain; (b) bringing into contact said receptor of (a) with a test molecule comprising a second group and said compound linked to each other, wherein said first group binds said second group; and (c) determining, subsequent to the binding of said first group to said second group, whether said compound binds to said target domain.

A target domain of a GPCR according to the invention may be any domain. The term "domain", as used in the art, refers to an autonomous folding unit which, if removed/cleaved from its context within a protein, maintains or substantially maintains its structure and functions. Domains of GPCRs include the transmembrane or juxtamembrane domain (J-domain), the extracellular domain, if present, which is involved in ligand binding and the intracellular domain, which is involved in signalling leading to cellular effects which may include the formation of one or more second messengers. Domain boundaries are well known to the skilled person and have been described for a number of GPCRs or can be determined from a sequence alignment, preferably a multiple sequence alignment, wherein domains correspond to regions of elevated sequence conservation or identity as compared to linkers, which exhibit a lower degree of sequence conservation or identity are not required for structural and/or functional integrity of isolated domains. Preferred target domains include the transmembrane and the extracellular domain. As regards class B GPCRs, which are preferred according to the invention (see below), Harmar (2001)[2] provides a multiple sequence alignment of transmembrane domains (FIG. 3 of Harmar (2001)) as well as of extracellular domains (FIG. 4 of Harmar (2001)), which are incorporated by reference. The sequences of the respective domains shown in Harmar (2001) (FIGS. 3 and 4) represent transmembrane and extracellular domains, respectively, suitable for the method of the present invention.

The term "receptor comprising said target domain" as used herein is to be held distinct from the specific GPCR the target domain is obtained or derived from. Said receptor comprising said target domain is the vehicle used for the screening method of the invention. It may comprise said target domain as the only proteinaceous component. As further detailed below, it may also comprise further domains obtained or derived from the same GPCR the target domain originates from or from a different GPCR. In the latter case, the receptor comprising said target domain is a chimeric receptor. Specific chimeric receptors are also subject of this invention (see below). The receptor of the invention may also comprise sequence which do not originate from a GPCR such as tags, GFP and leader sequences. It is furthermore deliberately envisaged that said receptor comprising said target domain is selected from naturally occurring GPCRs including class B GPCRs which are further detailed below.

The terms "extracellular" and "intracellular" as used herein relate to the positions of parts or domains of a receptor inserted in the membrane of an intact cell. However, also in the absence of a cell or membrane, these terms may be used to designate the corresponding parts or domains.

The terms "first group" and "second group" as used herein refer to any groups, provided they are capable of binding to each other. It is preferred that said binding is non-covalent. This applies to various preferred embodiments further detailed below.

Alternatively, said binding may be covalent. In this case, each compound to be assessed is part of a covalent construct comprising the receptor comprising said target domain, a group linked to said target domain, wherein said group in turn carries—via a covalent link—said compound to be assayed. In other words, the present invention also provides a method of identifying a compound capable of binding to a target domain of a G-protein coupled receptor comprising the steps of: (a) providing a receptor comprising said target domain and a group linked to said target domain, said group in turn being linked a compound; and (b) determining whether said compound binds to said target domain. The group linking target domain on the one side and compound on the other side may arise as a result of the formation of a covalent bond between a first and a second group. The ternary construct target domain—group—compound may be obtained by methods known in the art including the snap tag technology or the intein technology. In case of the snap tag technology said first group is an enzyme fused to said target domain, wherein the enzyme catalyses a reaction which leads to the formation of a covalent bond between the enzyme and said second group, which serves as a carrier group for said compound. The intein technology may in general be employed for ligating protein domains to each other in order to obtain constructs used in the screening method of the invention. Specifically it may be used, for example, for ligating a target domain to a first group and/or, in those cases where a covalent bond between first and second groups is desired, for ligating said first and second groups. It is understood that the intein technology is applicable where peptides or polypeptides are to be ligated. Both the snap tag method and the intein method are known in the art and described in, for example, Gronemeyer et al., Curr. Opin. Biotechnol. 16: 453-458 (2005) (as regards covalent labelling of fusion proteins including snap tag technology) and Muralidharan and Muir, Nature Methods 3: 429-438 (2006) (as regards protein ligation including intein-based methods).

First groups are also referred to as recruiting groups, whereas second groups are also referred to as carrier groups.

The link between said receptor and said first group may be any link. In case the first group is of a peptide or polypeptide, said link may be direct in that it is a peptide bond. This applies to embodiments where the first group is another domain of the GPCR the target domain originates from or of a different GPCR, as well as to embodiments wherein the first group is peptidic tag such as dicystein, tetracystein or a His tag. In these case said receptor can be subsumed under the term fusion protein and its preparation may be accomplished by molecular biology techniques without any need to further modify the expressed recombinant fusion protein. Alternatively to covalent links, non-covalent links are also envisaged. Suitable non-covalent links may be selected from the non-covalent interaction pairs described below as preferred embodiments of first and second groups, respectively.

Similarly, the link between said second group and said compound may be any link. Preferably, the link is covalent as further detailed below. However, also non-covalent links are deliberately envisaged. Suitable non-covalent links may be selected from the non-covalent interaction pairs described below as preferred embodiments of first and second groups, respectively. Preferably the link between said second group and said compound is such that said compound, when linked to said second group is in the same or substantially the same conformation as in its free form, i.e. without said second group linked to it. Suitable linkers are further detailed below.

The binding of said compound to said target domain may be a binding to any conformational state of said target domain. In other words, it may lead to any conformational state of said target domain. GPCRs and accordingly the receptor used in the method of the invention occur in at least two distinct states, an activated and an inactive state. The activated state is capable of eliciting signal transduction. Recently Hoare et al. (Hoare, S. R. J.; Sullivan, S. K.; Pahuja, A.; Ling, N.; Crowe, P. D.; Grigoriadis, D. E. *Peptides* 2003, 24, 1881-1897) have identified three different conformational states of $CRFR_1$, as well as the nature of two of them: a state in which the receptor is uncoupled to G-protein (R state) and another one in which the receptor is coupled to G-proteins (RG state): The nature of the third state named $R_0$ has also been detected in others B-GPCRs such as Parathyroid Hormone Receptor (PHTR) (see. Dean, T.; Linglart, A.; Mahon, M. J.; Bastepe, M.; Jüppner, H.; Potts, J. T.; Gardella, T. J. *Mol. Endicronol.* 2006, 20, 931-943). Some peptidic modulators of $CRFR_1$ are partially selective in the binding to those $CRFR_1$'s states.

Binding of said compound may or may not entail functional changes. In case it does, the binding may entail modulation of receptor function. Modulation may either be activation, in which case the method of the invention allows the identification of agonists or it may be de-activation, in which case the method of the invention allows the identification of antagonists. The precise nature of activation or de-activation processes depends on the read-out scheme used. Various read-out schemes are described in the prior art (cited below) and described further herein below.

The binding of said compound to the target domain or the interaction between said compound and the target domain occurs subsequent to the binding of the first and second groups to each other. As a consequence of the interaction between the first and second groups, the local concentration of the compound is increased and weaker binding compounds may be identified which otherwise would escape detection. Concomitantly, the total free energy of binding of the test molecule is elevated as compared to the free energy or binding of the compound alone.

The method of the present invention, instead of using conventional compound libraries, uses conjugates of high affinity binders (also referred to as second group or carrier group) with compounds of a library. This approach permits the detection of binding of compounds to the target domain which in the absence of the high affinity binder would not be possible. It exploits the two-domain model described for the signal transduction of peptidic ligands by class B1 GPCRs (FIG. 1A)[1].

In the field of class B GPCRs, chimeric receptor-ligand pairs and direct binding experiments with truncated/isolated domains[12] are consistent with a high-affinity interaction of the N-terminal extracellular domain of the receptor with the C-terminal, α-helical portion of the peptide ligand. This positions the N-terminal effector part of the peptide ligand in close proximity to the transmembrane J-domain, thereby inducing a structural rearrangement leading to G-protein activation. Chimeric receptors according to the invention permit to expand the two-domain model to non-class B GPCRs.

In an illustrative embodiment shown in FIG. 1B, peptide analogs derived from the high-affinity C-terminal domain of the native peptide ligands are linked to a library of fragments and these conjugates are used to probe receptor function in a high-throughput fashion. Thereby the effective concentration of the fragments is dramatically increased in the vicinity of the receptor J-domain, thereby allowing even very low-affinity interactions to be detected. After the identification of a few weakly binding fragments, analogs of these initial hits are prepared by classical medicinal chemistry to generate more potent low-molecular weight compounds that can be characterized by classical receptor assays wherein the low-molecular weight compounds are no longer linked to the peptide carrier (FIG. 1B). To the extent test molecules according to the invention comprise a fragment of a natural ligand, the method of the invention may also be referred to as biomimetic screening.

In a preferred embodiment, said target domain comprises or consists of the transmembrane or juxtamembrane domain of said G-protein coupled receptor or a fragment or analog thereof. Fragments include functional fragments, i.e. fragments which are capable of eliciting signal transduction. Assays for signal transduction are well known in the art further detailed below. Also included are fragments which comprise or consist of the seven transmembrane helices including the intervening intra- and extracellular loops (see, for example, FIG. 3 in reference 2).

The term "analog" as used herein in conjunction with peptides or polypeptides includes the replacement of one or more residues with non-naturally occurring amino acids as well as to constructs comprising protection groups. Non-naturally occurring amino acids include beta-alanine, alpha-amino butyric acid, gamma-amino butyric acid, alpha-amino isobutyric acid, norvaline, norleucine, epsilon-lysine, ornithine, homoserine and hydroxyproline. Up to 20% of the residues of the parent polypeptide may be replaced with non-naturally occurring amino acids, preferably up to 10%, 5% or 2%. Alternatively, more than 20% of the residues may be replaced. Also single replacement, which may correspond to less than 2% of the residues, are deliberately envisaged. The term "analog" also comprises peptidomimetics which are further detailed below.

The term "analog" as used throughout the specification preferably relates to functional analogs. Functional analogs include analogs which are capable of binding the respective cognate binding partner.

In a further preferred embodiment, said first group is linked to the extracellular part and/or the N-terminus of said transmembrane or juxtamembrane domain or a fragment or analog thereof. In case said first group is a peptide or polypeptide, it is preferred that said first group is fused, i.e. linked via a peptide bond, preferably via a main chain peptide bond, to said transmembrane or juxtamembrane domain or said fragment or analog thereof.

Preferably said first group comprises or consists of (i) the N-terminal domain of said G-protein coupled receptor or a fragment or analog thereof; (ii) the N-terminal domain of a different G-protein coupled receptor or a fragment or analog thereof; or (iii) avidin or biotin; a metal ion or chelator; a strep-tag or strep-tactin; glutathion or GST; tetracystein or diarsen. In case fragments of an N-terminal domain of a GPCR are to be used, the choice of the fragment boundaries may be done in conjunction with the choice of C-terminal part of a natural cognate ligand of said GPCR further detailed below, thereby ensuring that cognate first and second groups are provided which are capable of binding to each other. The receptor used as a vehicle for the screening method of the invention may comprise or consist of a fragment of a GPCR beginning with the N-terminal residue of said GPCR and ending with the last residue of the seventh transmembrane helix. In case the N-terminal domain of a different GPCR is used, said N-terminal domain may be fused to said transmembrane domain at any position in the sequence alignment where the sequences connecting the N-terminal domain and the transmembrane domain are aligned (see, for example, reference 2 as cited herein for multiple sequence alignments).

In a further preferred embodiment of the method of the invention, said second group comprises or consists of (i) the C-terminal part of a natural cognate ligand of said G-protein coupled receptor providing said N-terminal domain or a fragment or analog thereof capable of binding said N-terminal domain; or (ii) biotin or avidin; a metal ion or chelator; a strep-tag or strep-tactin; glutathion or GST; tetracystein or diarsen. Preferred length of fragments of said C-terminal part are between 5 and 40, more preferred between 10 and 30 or 10 and 20, most preferred between 10 and 12 residues. Preferably said fragments bind with a nanomolar binding constant to said N-terminal domain. Preferred binding constants are between 1 and 100 nM and include 5 nM as reported for the peptide described in Yamada et al.[16] The peptide described in Yamada et al. is a preferred second group of the invention. This peptide is shown in FIG. 2B; see also SEQ. ID NO: 27. Of course, more affine fragments are also deliberately envisaged. Higher affinity between first and second groups permits the detection of compounds binding to the target domain with even lower affinity. The term analog is defined herein above. Peptidomimetics, which also fall under the term "analog" according to the invention include alpha-helix mimetics such as substituted poly-p-phenylenes (e.g. terphenyls), oligoamides (e.g. trispyridylamides, terephthalamides), and beta-peptides. These compound classes and their suitability as peptidomimetics have been review in, for example, Fletcher and Hamilton, Curr. Opin. Chemical Biol. 9: 632-638 (2005). Preferred are conformationally restrained peptidomimetics, e.g. cyclic compounds. Fragments or analogs of said C-terminal part of a natural cognate ligand are known in the art and include peptides comprising or consisting of the sequences set forth in any one of SEQ ID NOs: 1 to 3, [Leu$^{11}$,D-Trp$^{12}$]PTHrP(7-34) (see Example 3), [Ile$^5$,Trp$^{23}$, Tyr$^{36}$]PTHrP(5-36) (see Example 3), and a peptide consisting of the sequence of any one of secretin, VIP, PACAP, glucagon, GHRH, GLP-1, GLP-2, GIP, CRF, urocortin, urocortin II, urocortin III, parathyroid hormone, PTH-related peptide, TIP39, calcitonin gene related peptide, adrenomedullin, calcitonin, amylin or CGRP, wherein between 1 and 10 N-terminal amino acids are deleted from said peptide, or a sequence having at least 70% sequence identity to the truncated peptide. Exemplary sequences of natural ligands (SEQ ID NOs: 4 to 24) are shown in Example 3.

In an alternative preferred embodiment of the main embodiment, said target domain comprises or consists of the extracellular or N-terminal domain of said G-protein coupled receptor or a fragment or analog thereof. In conjunction with this embodiment, said first group preferably comprises or consists of (i) the transmembrane or juxtamembrane domain of said G-protein coupled receptor or a fragment or analog thereof; or (ii) the transmembrane or juxtamembrane domain of a different G-protein coupled receptor or a fragment or analog thereof. More preferably, said second group comprises or consists of the N-terminal part of a natural cognate ligand of said G-protein coupled receptor or a fragment or analog thereof capable of binding and/or activating said transmembrane or juxtamembrane domain or fragment or analog thereof. Embodiments of the invention wherein the N-terminal domain of a GPCR is used as target domain for the screen are also referred to as "reverse setup".

The reverse setup also includes embodiments, wherein the binding of first and second group does not occur prior to binding of the compound to the target domain. Instead, binding of first and second group may serve as a read-out to identify compounds binding to the target domain. In other words, the invention also provides a method of identifying a compound capable of binding to the N-terminal domain of a G-protein coupled receptor or a fragment or analog thereof comprising the steps of: (a) providing a receptor comprising said N-terminal domain or fragment or analog thereof and a first group linked thereto; (b) bringing into contact said receptor of (a) with a test molecule comprising a second group and said compound linked to each other, wherein said first group is capable to bind said second group; and (c) determining whether said compound binds to said target domain, wherein said determining is effected by determining binding of said first and second groups.

In a further preferred embodiment, said G-protein coupled receptor is a class B G-protein coupled receptor. The class B of GPCRs is also referred to as type II or secretin class. These terms are well known to the skilled person. Class B GPCRs are reviewed in, for example, references 1 and 2 cited herein. Preferably, said class B G-protein coupled receptor is selected from the group consisting of corticotropin releasing factor receptors CRFR1, CRFR2a, CRFR2b and CRFR2c; parathyroid hormone receptors PTHR1 and PTHR2; glucagon receptor (GCGR); growth hormone releasing hormone receptor (GHRHR); glucagon-related peptide receptors GLP1R and GLP2R; gastric inhibitory polypeptide receptor (IPR); secretin receptor (SCTR); calcitonin receptor (CALCR); calcitonin receptor-like receptor (CALCRL); vasoactive intestinal peptide receptors VIPR1 and VIPR2; and adenylate cyclase activating polypeptide 1 receptor (ADCYAP1R1) (see also reference 2). The terms in brackets are common abbreviations. Abbreviations which are not in brackets refer to specific members of a family, e.g. CRFR1 is a member of the family of corticotropin releasing factor receptors.

In a further preferred embodiment, said compound is a peptide, peptidomimetic or a small organic molecule. The term "peptidomimetic is defined herein above.

Preferably, said compound has a molecular weight below 300 Da.

More preferably, said compound has a molecular weight between 200 and 250 Da.

Since the method of the invention allows detection of weak binders to the target domain, compounds may be employed with a molecular weight below the average molecular weight of compounds of a conventional screening library. Such compounds of lower molecular weight are also referred to as fragments. As stated above, fragments exhibit properties rendering them superior to larger molecules. These properties include: (i) Due to their small size, fragments provide a better coverage of the respective chemical space[7]; (ii) fragments have a higher probability to fit into a given binding pocket[8]; and (iii) fragments are likely to have a better binding energy/heavy atom ratio (ligand efficiency)[9] thus making them better starting points for a drug development process.

In another preferred embodiment, the method of the invention further comprises the step of (d) optimising the binding of said compound to said target domain, wherein said compound is devoid of said second group.

Methods for the optimization of the pharmacological properties of compounds identified in screens, generally referred to as lead compounds, are known in the art and comprise a method of modifying a compound identified as a lead compound to achieve: (i) improved affinity to the target domain, (ii) modified site of action, spectrum of activity, organ specificity, and/or (iii) improved potency, and/or (iv) decreased toxicity (improved therapeutic index), and/or (v) decreased side effects, and/or (vi) modified onset of therapeutic action, duration of effect, and/or (vii) modified pharmacokinetic parameters (resorption, distribution, metabolism and excretion), and/or (viii) modified physico-chemical parameters (solubility, hygroscopicity, color, taste, odor, stability, state), and/or (ix) improved general specificity, organ/tissue specificity, and/or (x) optimized application form and route.

One or more of these aims are achieved by (i) esterification of carboxyl groups, or (ii) esterification of hydroxyl groups with carboxylic acids, or (iii) esterification of hydroxyl groups to, e.g. phosphates, pyrophosphates or sulfates or hemi-succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetates, or (xiv) N-acetylation to amides, phenylcarbamates, or (xv) synthesis of Mannich bases, imines, or (xvi) transformation of ketones or aldehydes to Schiff's bases, oximes, acetates, ketales, enolesters, oxazolidines, thiazolidines or combinations thereof.

The various steps recited above are generally known in the art. They include or rely on quantitative structure-action relationship (QSAR) analyses (Kubinyi, "Hausch-Analysis and Related Approaches", VCH Verlag, Weinheim, 1992), combinatorial biochemistry, classical chemistry and others (see, for example, Holzgrabe and Bechtold, Deutsche Apotheker Zeitung 140(8), 813-823, 2000).

Preferably, the method of the invention further comprises the steps of (e) bringing into contact of said receptor with said compound identified in step (c) or optimised in the step (d), wherein said compound is devoid of said second group; and (f) determining whether said compound being devoid of said second group binds to said target domain. For the purposes of this embodiment, the first group may be absent from the receptor, noting that the test molecule to be assayed consists of the compound only.

In a preferred embodiment, said determining in step (c) or step (f) is effected by determining displacement of a labelled reference compound known to bind the target domain. Said reference compound, in those cases where both target domain and first group originate from the same GPCR, may be the natural ligand of the GPCR or an analog or fragment thereof. In case the receptor used in the screen is a chimeric receptor, for example a receptor comprising a transmembrane domain from one GPCR and an N-terminal domain from another GPCR, matching chimeric reference compounds may be prepared. Said chimeric reference compounds comprise or consist of a part capable of binding to the first group and a second part capable of binding to the target domain. Alternatively, the reference compound may bind only to the target domain and hot to the first group. N-terminal fragments of peptidic ligands of GPCRs or analogs thereof may be used in this case. Such fragments are known in the art and further detailed below. Furthermore, non-peptidic reference compound may be used. Examples include 3H-NBI35965 (Hoare, Mol. Pharmacol. (2003), 751-765) and 3H-SN003 (Zhang, J. Pharmacol. Exp. Therapeut. (2003), 57-69), which are both suitable reference compounds in particular for CRFR1. Furthermore, natural ligands may be used as reference compounds. Examples of natural ligands include (in brackets the abbreviation of the cognate receptor): secretin (SCTR); VIP and PACAP (VIPR1, VIPR2); PACAP (ADCYAPIR1); glucagon (GCGR); GHRH (GHRHR); GLP-1 (GLP1R); GLP-2 (GLP2R); GIP (GIPR); CRF and urocortin (CRHR1); urocortin, urocortin II, urocortin III and perhaps CRF (CRHR2), parathyroid hormone and PTH-related peptide (PTHR1); TIP39 (PTHR2); calcitonin gene related peptide and adrenomedullin (CALCRL); calcitonin, amylin and CGRP (CALCR) (see also Table 1 of Harmar (2001) (reference 2)). These examples relate to the class B GPCRs which are preferred according to the invention. A further example of a reference compound is $^{I125}Tyr_0$-sauvagine. Exemplary sequences of further natural ligands (SEQ ID NOs: 4 to 24) which are suitable reference compounds are shown in Example 3. Any label, including fluorescent, luminescent and radioactive labels may be used to facilitate detection of the reference compound.

Alternatively or additionally, said determining in step (c) or step (f) is effected by determining whether a conformational or functional change of said target domain occurs, said change being indicative of a compound binding to said target domain. A variety of assays directed to the monitoring of conformational and/or functional changes of GPCR-derived target domains is known in the art and described in, for example, Thomsen et al., Curr. Opin. Biotechnol., 16: 655-665 (2005); Greasley and Jansen, Drug Discovery Today: Technologies 2: 163-170 (2005); and Milligan, Drug Discovery Today 8: 579-585 (2003). A number of specific preferred assays is further detailed below.

Preferably, said receptor according to the invention comprises the C-terminal domain of said G-protein coupled receptor or of a different G-protein coupled receptor or a fragment of said C-terminal domain, wherein said fragment is capable of initiating signal transduction. The presence of the C-terminal domain implies presence of the transmembrane domain. This embodiment is of particular relevance for those read-out schemes which involve parts of the signal transduction pathway triggered by an activated GPCR in its natural environment. A naturally occurring GPCR may also be used. Said naturally occurring GPCR, preferably a class B GPCR provides an N-terminal domain and a transmembrane domain as first group and target domain, respectively (or vice versa in the framework of the reverse setup described above) as well as a C-terminal domain which is capable of triggering signal transduction.

More preferably, said determining in said steps (c) and/or (f) is effected by determining (i) the formation of a secondary messenger; (ii) the displacement of a GTP analog; (iii) covalent modification of said receptor such as phosphorylation; or (iv) recruiting of an interaction partner of said receptor such as arrestin or a G-protein. The term "displacement of a GTP analog" refers to a read-out at the G-protein level. Receptor phosphorylation in known to occur in response to a change of receptor status, for example, activation of the receptor in response to binding of a compound. The term "interaction partner of said receptor" relates to molecules which bind a certain conformation (usually the active conformation) of the receptor and do not bind another conformation (usually the inactive conformation). Such interaction partners are well known in the art and include G-protein as well as engineered G-proteins and arrestin.

Preferred secondary messengers are selected from the group consisting of cAMP, inositol trisphosphate and $Ca^{2+}$. Detection schemes for secondary messengers including the preferred secondary messengers described above are well known in the art (see, for example, Williams, Nature Reviews Drug Discovery 3: 125-135 (2004)). Methods/assays according to the invention where a secondary messenger is to be detected comprise the required components of the signal transduction pathway which are well known in the art. For example, in case of cAMP formation to be detected or monitored, a G protein, adenlyate cyclase and ATP are present.

In a further preferred embodiment, (i) said receptor comprises (an) additional group(s) sensitive to said conformational change; and (ii) said determining in said steps (c) and/or (f) is effected by determining a parameter of said additional group(s). Preferably, said additional group(s) is/are selected from groups detectable by spectroscopic means, and wherein said parameter is the absorption and/or emission characteristic of said additional group(s).

More preferably, said additional group(s) is/are a FRET pair or a BRET pair. The term FRET designates fluorescence resonance energy transfer and refers to the transfer of energy between two fluorophores. BRET designates the analogous phenomenon between bioluminescent moieties (see for example, Hoffmann, Nat. Methods (2005) 171-176; and Gales, Nat. Methods (2005), 177-184).

In a preferred embodiment, the fluorophores are selected from the group consisting of fluorenes, pyrenes, xanthenes including, rhodamines, coumarins, naphthylamines, acridines, benzoxazoles, benzodioxazoles, stilbenes, poly(p-phenylene vinylene)s, polythiophenes, poly(phenylene ethynylene)s and poly(para-phenylene)s. Naphthylamines may have the amino group in the alpha or beta position and include 1-dimethylaminonaphthyl-5-sulfonate, 1-anilino-8-naphthalene sulfonate and 2-p-toluidinyl-6-naphthalene sulfonate. Coumarins include 3-phenyl-7-isocyanatocoumarin; acridines include 9-isothiocyanatoacridine and acridine orange; and benzoxazoles include N-(p-(2-benzoxazolyl) phenyl)maleimide.

It is understood that the use of the plural form, such as "fluorenes", indicates that not only fluorene itself, but also derivatives thereof known in the art at the priority date of the instant application are embraced.

Specific fluorophores according to the invention include the following commercially available (for example from Synthegen) fluorescent dyes: Tamra-dT, 5-Fluorescein (FITC), 5-Carboxyfluorescein (FAM), 6-Carboxyfluorescein (FAM), 3' 6-Carboxyfluorescein (FAM), 6-Carboxyfluorescein-DMT (FAM-X), 5(6)-Carboxyfluorescein (FAM), 6-Hexachlorofluorescein (HEX), 6-Tetrachlorofluorescein (TET), JOE, LightCycler Red 640, LightCycler Red 705, FAR-Fuchsia (5'-Amidite), FAR-Fuchsia (SE), FAR-Blue (5'-Amidite), FAR-Blue (SE), FAR-Green One (SE), FAR-Green Two (SE), Oregon Green 488, Oregon Green 500, Oregon Green 514, BODIPY FL-X, BODIPY FL, BODIPY-TMR-X, BODIPY R6G, BODIPY 650/665, BODIPY 564/570, BODIPY 581/591, BODIPY TR-X, BODIPY 630/650, BODIPY 493/503, Carboxyrhodamine 6G, MAX, 5(6)-Carboxytetramethylrhodamine (TAMRA), 6-Carboxytetramethylrhodamine (TAMRA), 5(6)-Carboxy-X, Rhodamine (ROX), 6-Carboxy-X-Rhodamine (ROX), AMCA-X (Coumarin), Texas Red-X, Rhodamine Red-X, Marina Blue, Pacific Blue, Rhodamine Green-X, 7-diethylaminocoumarin-3-carboxylic acid, 7-methoxycoumarin-3-carboxylic acid, Cy3, Cy3B, Cy5, Cy5.5, DY-505, DY-550, DY-555, DY-610, DY-630, DY-633, DY-636, DY-650, DY-675, DY-676, DY-681, DY-700, DY-701, DY-730, DY-750, DY-751, DY-782, Cy3.5 and EDANS.

For FRET or BRET to occur, the emission spectrum of the emitting moiety and the absorption spectrum of the absorbing moiety have to overlap. The skilled person is able to selected suitable pairs of fluorophores or bioluminescent groups without further ado, based on the absorption and emission characteristics and/or information from the manufacturer.

In a further preferred embodiment, said receptor is located in the membrane of a cell. Preferably, said cell is an intact cell and provides the downstream effectors of said receptor. This embodiment relates to a cellular screen. Any cell which either naturally expresses a receptor according to the invention or which has been genetically modified to do so is suitable for the method of the invention. Depending on the read-out scheme used, said cell may further comprise components of the GPCR signal transduction pathway.

Preferably, said additional group is (i) a tag capable of binding a cognate antibody; or (ii) an enzyme fused to said target domain.

In preferred embodiments of the cellular screen of the invention, said determining in said steps (c) and/or (f) is effected by determining cellular dynamics.

Said cellular dynamics is preferably selected from (i) arrestin translocation; and (ii) internalisation of the receptor of the invention.

In a further preferred embodiment, said receptor is (i) solubilized; or (ii) located in a membrane of a micelle or a membrane preparation. Preferably, the solubilization is a functional solubilization, i.e., the function of said receptor is maintained upon solubilization, thereby permitting functional read-out schemes as described herein. Functional solubilization may be effected by mild detergents such as non-ionic detergents.

The linker between said target domain and said first group and/or the linker between said second group and said compound is preferably selected from the group consisting of alkyl with 1 to 30 carbon atoms, polyethylene glycol with 1 to 20 ethylene moieties, polyalanine with 1 to 20 residues, caproic acid, substituted or unsubstituted poly-p-phenylene and triazol. An exemplary linker and its synthesis is shown in Example 4. The linker of Example 4 is not yet attached to any one of said target domain, said first and second group, and said compound. Accordingly this linker has two terminal functionalities for attaching it to any one of said target domain, said first and second group, and said compound. In the special case of this Example, these functionalities are azide and carboxylate (see compound 4 of Example 4).

In a further preferred embodiment, said linker is selected from the group consisting of amino-n-alkyl, mercapto-n-alkyl, amino-n-alkyl-X-alkyl, mercapto-n-alkyl-X-alkyl, wherein X is selected from the group consisting of O, S—S and $SO_2$ and wherein the alkyl groups independently from each other have from 1 to 30 carbon atoms, preferably 3, 6 or 12 carbon atoms; or oligoethylenglycols having from one to about ten ethylenglycol moieties, preferably tri- or hexa-ethylenglycol.

These and further suitable linkers are well known in the art and commercially available (see, for example, the catalogue from Glen Research, 22825 Davis Drive, Sterling, Va., 20164 USA). Further examples of linkers are the following: 5'-Amino-Modifiers (see e.g. B. A. Connolly and P. Rider, Nucleic Acids Res., 1985, 13, 4485; B. S. Sproat, B. S. Beijer, P. Rider, and P. Neuner, Nucleic Acids Res., 1987, 15, 4837; R. Zuckerman, D. Corey, and P. Shultz, Nucleic Acids Res., 1987, 15, 5305; P. Li, et al., Nucleic Acids Res., 1987, 15, 5275; G. B. Dreyer and P. B. Dervan, Proc. Natl. Acad. Sci. USA, 1985, 82, 968.); 5'-Thiol-Modifier C6 (see e.g. B. A. Connolly and P. Rider, Nucleic Acids Res., 1985, 13, 4485; B. S. Sproat, B. S. Beijer, P. Rider, and P. Neuner, Nucleic Acids Res., 1987, 15, 4837; R. Zuckerman, D. Corey, and P. Shultz, Nucleic Acids Res., 1987, 15, 5305; P. Li, et al., Nucleic Acids Res., 1987, 15, 5275.); 5'-Thiol-Modifier C6 S—S and Thiol Group at the 3'-Terminus (see e.g. B. A. Connolly and R. Rider, Nucleic Acids Res., 1985, 13, 4485; B. A. Connolly, Nucleic Acids Res., 1987, 15, 3131-3139; N. D. Sinha and R. M. Cook, Nucleic Acids Res., 1988, 16, 2659; A. Kumar, S. Advani, H. Dawar, and G. P. Talwar, Nucleic Acids Res., 1991, 19, 4561; R. Zuckermann, D. Corey, and P. Schultz, Nucleic Acids Res., 1987, 15, 5305; K. C. Gupta, P. Sharma, S. Sathyanarayana, and P. Kumar, Tetrahedron Lett., 1990, 31, 2471-2474; U. Asseline, E. Bonfils, R. Kurfurst, M. Chassignol, V. Roig, and N. T. Thuong, Tetrahedron, 1992, 48, 1233-1254; Gregg Morin, Geron Corporation, Personal Communication.); Spacer C3, Spacer C12, and dSpacer Phosphoramidites (see e.g. M. Durard, K. Chevrie, M. Chassignol, N. T. Thuong, and J. C. Maurizot, Nucleic Acids Res., 1990, 18, 6353; M. Salunkhe, T. F. Wu, and R. L. Letsinger, J. Amer. Chem. Soc., 1992, 114, 8768-8772; N. G. Dolinnaya, M. Blumenfeld, I. N. Merenkova, T. S. Oretskaya, N. F. Krynetskaya, M. G. Ivanovskaya, M. Vasseur, and Z. A. Shabarova, Nucleic Acids Res., 1993, 21, 5403-5407; M. Takeshita, C. N. Chang, F. Johnson, S. Will, and A. P. Grollman, J. Biol. Chem., 1987, 262, 10171-10179; M. W. Kalnik, C. N. Chang, A. P. Grollman, and D. J. Patel, Biochemistry, 1988, 27, 924-931.); 3'-Amino-Modifier C7 CPG (see e.g. J. G. Zendegui, K. M. Vasquez, J. H. Tinsley, D. J. Kessler, and M. E. Hogan, Nucleic Acids Res., 1992, 20, 307.); 3'-Amino Photolabile C6 CPG (see e.g. D. J. Yoo and M. M. Greenberg, *J. Org. Chem.*, 1995, 60, 3358-3364.; H. Venkatesan and M. M. Greenberg, *J. Org. Chem.*, 1996, 61, 525-529; D. L. McMinn and M. M. Greenberg, *Tetrahedron,* 1996, 52, 3827-3840.

A linker according to the invention may also comprise or consist of two or more of the abovedescribed specific linkers. For example, and as shown in compound 9 of Example 6, a linker may consist of triazol attached to a polyethylene glycol.

The present invention also relates to a kit comprising a library of test molecules, wherein each test molecule comprises or consists of (i) a peptide comprising or consisting of the sequence of any one of SEQ ID NO: 1 to 3, or a sequence having at least 70% sequence identity to said sequence of any one of SEQ ID NO: 1 to 3, linked to (ii) a member of a library of compounds; wherein (iii) the linker is selected from the group consisting of alkyl with 1 to 30 carbon atoms, polyethylene glycol with 1 to 20 ethylene moieties, polyalanine with 1 to 20 residues, caproic acid, substituted or unsubstituted poly-p-phenylene and triazol. Further preferred linkers are described herein above. More preferred, the above-mentioned sequence identity is 80%, 85%, 90%, 95%, 98% or 99%. Preferably, the linker is at the N-terminus of said peptide. It is understood that naturally occurring GPCR ligands are excluded from the compounds of the kit of the invention. An exemplary test molecule is compound 9, the synthesis of which is shown in Example 6. A further exemplary test molecule is shown in FIG. 2A.

In a further embodiment relating to a kit, the sequence of any one of SEQ ID NO: 1 to 3 is replaced with an N-terminally truncated form of a natural ligand of a GPCR. It is known in the art and further exemplified in Example 3 and the references cited therein that truncation of natural cognate peptide ligands yields an antagonist, i.e., a compound binding to the cognate GPCR without activating it. Preferred truncation is by removal of between 1 and 20, more preferred between 1 and 15 and yet more preferred between 1 and 10 residues. Any intervening number of N-terminal amino acids to be removed, such as 2, 3, 4, 5, 6, 7, 8, 9 is deliberately envisaged. Also, removal of 11, 12, 13, 14, 16, 17, 18 or 19 amino acids from the N-terminal of the natural ligand is encompassed. Natural ligands include (in brackets the abbreviation of the cognate receptor): secretin (SCTR); VIP and PACAP (VIPR1, VIPR2); PACAP (ADCYAPIR1); glucagon (GCGR); GHRH (GHRHR); GLP-1 (GLP1R); GLP-2 (GLP2R); GIP (GIPR); CRF and urocortin (CRHR1); urocortin, urocortin II, urocortin III and perhaps CRF (CRHR2), parathyroid hormone and PTH-related peptide (PTHR1); TIP39 (PTHR2); calcitonin gene related peptide and adrenomedullin (CALCRL); calcitonin, amylin and CGRP (CALCR) (see also Table 1 of Harmar (2001) (reference 2)). In a preferred embodiment, said truncated peptides are subjected to optimisation, in particular of their affinity for the target domain. Means and methods for optimisation are well known in the art and further detailed above.

Therefore, the present invention also relates to a kit comprising a library of test molecules, wherein each test molecule comprises or consists of (i) a peptide consisting of the sequence of any one of secretin, VIP, PACAP, glucagon, GHRH, GLP-1, GLP-2, GIP; CRF, urocortin, urocortin II, urocortin III, parathyroid hormone, PTH-related peptide, TIP39, calcitonin gene related peptide, adrenomedullin, calcitonin, amylin or CGRP, wherein between 1 and 10 N-terminal amino acids are deleted from said peptide, or a sequence having at least 70% sequence identity to the truncated peptide, or an analog thereof, linked to (ii) a member of a library of compounds; wherein (iii) the linker is selected from the group consisting of alkyl with 1 to 30 carbon atoms, polyethylene glycol with 1 to 20 ethylene moieties, polyalanine with 1 to 20 residues, caproic acid, substituted or unsubstituted poly-p-phenylene and triazol. Preferably, the linker is at the N-terminus of said peptide. Again, it is understood that naturally occurring GPCR ligands are excluded from the compounds of the kit of the invention. The term "analog" is defined herein above. The above recited analog of a truncated peptide is preferably an analog capable of binding to said first group of said receptor according to the invention.

In a further embodiment relating to a kit, the sequence of any one of SEQ ID NO: 1 to 3 is replaced with [Leu$^{11}$,D-Trp$^{12}$]PTHrP(7-34) (see Example 3), [Ile$^5$,Trp$^{23}$, Tyr$^{36}$]PTHrP(5-36) (see Example 3).

Preferably said kit further comprises the receptor according to the invention. As stated above, the term "receptor" is to be held distinct from a naturally occurring GPCR and instead relates to the vehicle used for the identification of binding/interacting compounds. Nevertheless, and as stated above, the term "receptor" comprises also naturally occurring GPCRs as well as functional fragments thereof.

Figure 5:
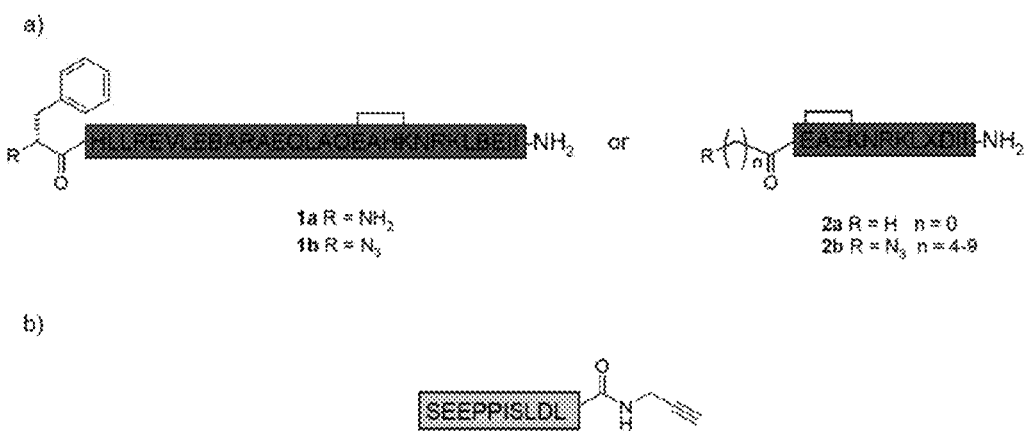

The present invention also provides a compound comprising or consisting of (i) a peptide comprising or consisting of the sequence of any one of SEQ ID NO: 1 to 3, or a sequence having at least 70% sequence identity to said sequence of any one of SEQ ID NO: 1 to 3, said peptide being linked to (ii) a first reactive group, wherein (iii) the linker is selected from the group consisting of alkyl with 1 to 30 carbon atoms, polyethylene glycol with 1 to 20 ethylene moieties, polyalanine with 1 to 20 residues, caproic acid, substituted or unsubstituted poly-p-phenylene and triazol. Further preferred linkers are described herein above. This compound is capable of binding to a first group as defined herein above, preferably a first group which is an N-terminal domain of a GPCR, and is also referred to as precursor herein, noting that it is a precursor of a test molecule according to the invention. It is to be held distinct from the compound according to the main embodiment which is a compound potentially binding to a target domain according to the invention. An exemplary precursor compound is compound 5 of Example 5. Compound 5 is a variant of compound 2b as shown in FIG. 5. In particular, the amino acid sequence of compound 2b of FIG. 5 is N-terminally extended by one amino acid. This amino acid may be any amino acid. In compound 5 it has been chosen to be Gln.

Furthermore, the present invention also relates to a compound comprising or consisting of (i) a peptide consisting of the sequence of any one of secretin, VIP, PACAP, glucagon, GHRH, GLP-1, GLP-2, GIP, CRF, urocortin, urocortin II, urocortin III, parathyroid hormone, PTH-related peptide, TIP39, calcitonin gene related peptide, adrenomedullin, calcitonin, amylin or CGRP, wherein between 1 and 10 N-terminal amino acids are deleted from said peptide, or a sequence having at least 70% sequence identity to the truncated peptide, or an analog thereof, linked to (ii) a member of a library of compounds; wherein (iii) the linker is selected from the group consisting of alkyl with 1 to 30 carbon atoms, polyethylene glycol with 1 to 20 ethylene moieties, polyalanine with 1 to 20 residues, caproic acid, substituted or unsubstituted poly-p-phenylene and triazol. Further preferred linkers are described herein above. Preferably, the linker is at the N-terminus of said peptide. Again, it is understood that naturally occurring GPCR ligands are excluded from the compounds of the invention. The term "analog" is defined herein above. The above recited analog of a truncated peptide is preferably an analog capable of binding to said first group of said receptor according to the invention.

In a further embodiment relating to a precursor compound, a compound is provided which comprises or consists of (i) [Leu$^{11}$,D-Trp$^{12}$]PTHrP(7-34) or [Ile$^5$,Trp$^{23}$, Tyr$^{36}$]PTHrP(5-36), linked to (ii) a member of a library of compounds; wherein (iii) the linker is selected from the group consisting of alkyl with 1 to 30 carbon atoms, polyethylene glycol with 1 to 20 ethylene moieties, polyalanine with 1 to 20 residues, caproic acid, substituted or unsubstituted poly-p-phenylene and triazol.

Also provided is a method of producing a test molecule according to the invention, wherein said method comprises reacting a precursor compound defined above and a compound selected from peptide, peptidomimetic and small organic molecule, wherein said peptide, peptidomimetic and small organic molecule carries a second reactive group.

Preferably, said first and/or said second reactive group is selected from the group consisting of thiol, amine, alkyne, azide, aldehyde, activated ester, phosphor ylide, hydroxylamine, alpha-halogen carboxamide/carboxylester, alpha, beta-unsaturated carbonyls, activated disulfides, Michael acceptor, Michael donor, diene and dienophile. Activated esters include NHS, pentafluorophenyl and p-nitrophenylesters. Preferably, the halogen in said alpha-halogen carboxamide/carboxylester is Cl, Br or I. Activated disulfides include the 2-thiopyridinyl group. The skilled person is capable of selecting matching pairs of first and second reactive groups without further ado.

Also provided is a chimeric G-protein coupled receptor comprising or consisting of (i) a class A or a class C G-protein coupled receptor or a fragment thereof comprising or consisting of the transmembrane or juxtamembrane domain thereof fused or linked to (ii) the N-terminal domain of a class B G-protein coupled receptor or a fragment of said N-terminal domain, wherein said fragment is capable of binding the C-terminal part of a natural cognate ligand of said class B G-protein coupled receptor. Sequences of N-terminal domains of class B GPCRs can be taken from FIG. 4 of reference 2. Suitable transmembrane domains may begin with the first residue of the first transmembrane helix and end with the last residue of the seventh transmembrane helix.

Further embodiments relate to a membrane preparation comprising said chimeric G-protein coupled receptor and a nucleic acid or polynucleotide encoding said chimeric G-protein coupled receptor. The latter embodiment of the invention relates to those cases Wherein said chimeric G-protein coupled receptor is a fusion protein.

Finally, a vector comprising said nucleic acid and a cell transformed with said vector or said nucleic acid is provided.

Preferably, the said vector is a plasmid, cosmid, virus, bacteriophage or another vector used e.g. conventionally in genetic engineering.

The nucleic acid or polynucleotide of the present invention may be inserted into several commercially available vectors. Non-limiting examples include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Intvitrogen).

The nucleic acid or polynucleotide of the present invention referred to above may also be inserted into vectors such that a translational fusion with another polynucleotide is generated. The other polynucleotide may encode a protein which may e.g. increase the solubility and/or facilitate the purification of the fusion protein. Non-limiting examples include pET32, pET41, pET43. The vectors may also contain an additional expressible polynucleotide coding for one or more chaperones to facilitate correct protein folding. Suitable bacterial expression hosts comprise e.g. strains derived from BL21 (such as BL21(DE3), BL21(DE3)PlysS, BL21(DE3)RIL, BL21(DE3)PRARE) or Rosetta®.

For vector modification techniques, see Sambrook and Russel (2001), loc. cit. Generally, vectors can contain one or more origin of replication (ori) and inheritance systems for cloning or expression, one or more markers for selection in the host, e.g., antibiotic resistance, and one or more expression cassettes. Suitable origins of replication (ori) include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions. Preferably, the polynucleotide of the invention is operatively linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the polynucleotide of the invention. Such leader sequences are well known in the art.

Possible examples for regulatory elements ensuring the initiation of transcription comprise the cytomegalovirus (CMV) promoter, SV40-promoter, RSV-promoter (Rous sarcome virus), the lacZ promoter, the gai10 promoter, human elongation factor 1α-promoter, CMV enhancer, CaM-kinase promoter, the *Autographa californica* multiple nuclear polyhedrosis virus (AcMNPV) polyhedral promoter or the SV40-enhancer. For the expression in prokaryotes, a multitude of promoters including, for example, the tac-lac-promoter, the lacUV5 or the trp promoter, has been described. Examples for further regulatory elements in prokaryotes and eukaryotic cells comprise transcription termination signals, such as SV40-poly-A site or the tk-poly-A site or the SV40, lacZ and AcMNPV polyhedral polyadenylation signals, downstream of the polynucleotide.

Furthermore, it is preferred that the vector of the invention comprises a selectable marker. Examples of selectable markers include neomycin, ampicillin, and hygromycine, kanamycine resistance and the like. Specifically-designed vectors allow the shuttling of DNA between different hosts, such as bacteria-fungal cells or bacteria-animal cells (e.g. the Gateway® system available at Invitrogen).

An expression vector according to this invention is capable of directing the replication, and the expression, of the polynucleotide and encoded enzyme of this invention. Suitable expression vectors which comprise the described regulatory elements are known in the art such as Okayama-Berg cDNA expression vector pcDV1 (Pharmacia), pRc/CMV, pcDNA1, pcDNA3 (In-Vitrogene, as used, inter alia in the appended examples), pSPORT1 (GIBCO BRL) or pGEMHE (Promega), or prokaryotic expression vectors, such as lambda gt11, pJOE, the pBBR1-MCS—series, pJB861, pBSMuL, pBC2, pUCPKS, pTACT1 or, preferably, the pET vector (Novagen).

The nucleic acid molecules of the invention as described herein above may be designed for direct introduction or for introduction via liposomes, phage vectors or viral vectors (e.g. adenoviral, retroviral) into the cell. Additionally, baculoviral systems or systems based on Vaccinia Virus or Semliki Forest Virus can be used as eukaryotic expression system for the nucleic acid molecules of the invention.

A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropylthiol-b-D-galactoside. ("IPTG"). For recombinant expression and secretion, the polynucleotide of interest may be ligated between e.g. the PelB leader signal, which directs the recombinant protein in the periplasm and the gene III in a phagemid called pHEN4 (described in Ghahroudi et al, 1997, FEBS Letters 414:521-526). Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells. Alternatively, the recombinant (poly)peptide can be expressed in stable cell lines that contain the gene construct integrated into a chromosome. The co-transfection with a selectable marker such as dhfr, gpt, neomycin, hygromycin allows the identification and isolation of the transfected cells. The transfected nucleic acid can also be amplified to express large amounts of the encoded (poly)peptide. The DHFR (dihydrofolate reductase) marker is useful to develop cell lines that carry several hundred or even several thousand copies of the gene of interest. Another useful selection marker is the enzyme glutamine synthase (GS) (Murphy et al. 1991, *Biochem J.* 227:277-279; Bebbington et al. 1992, *Bio/Technology* 10:169-175). Using these markers, the mammalian cells are grown in selective medium and the cells with the highest resistance are selected. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS, 293 and Bowes melanoma cells; and plant cells. Appropriate culture mediums and conditions for the above-described host cells are known in the art.

The present invention also relates to a cell, genetically engineered with the nucleic acid or polynucleotide of the present invention or the vector of the present invention. The cell may be in cell culture or part of a host, wherein human hosts are excluded. Said cell or said host may be produced by introducing said polynucleotide or vector(s) into a cell or host which upon its/their presence mediates the expression of the polypeptide encoded by said nucleic acid or polynucleotide. The cell or host may be any prokaryote or eukaryotic cell. The description of hosts below applies mutatis mutandis, and where applicable, to cells according to the present invention. A suitable eukaryotic host may be a mammalian cell, an amphibian cell, a fish cell, an insect cell, a fungal cell or a plant cell. A eukaryotic cell may be an insect cell such as a *Spodoptera frugiperda* cell, a yeast cell such as a *Saccharomyces cerevisiae* or *Pichia pastoris* cell, a fungal cell such as an *Aspergillus* cell or a vertebrate cell. In the latter regard, it is preferred that the cell is a mammalian cell such as a human cell. The cell may be a part of a cell line.

The host may be any prokaryote or eukaryotic cell. A suitable eukaryotic host may be a mammalian cell, an amphibian cell, a fish cell, an insect cell, a fungal cell or a plant cell.

Suitable prokaryotes/bacteria are those generally used for cloning like *E. coli* (e.g., *E coli* strains HB101, DH5a, XL1 Blue, Y1090 and JM101), *Salmonella typhimurium, Serratia marcescens, Burkholderia glumae, Pseudomonas putida, Pseudomonas fluorescens, Pseudomonas stutzeri, Streptomyces lividans, Lactococcus lactis, Mycobacterium smegmatis* or *Bacillus subtilis*. Preferred examples for hosts to be genetically engineered with the polynucleotide of the invention are *E. coli* and *B. subtilis*.

In a preferred embodiment of the present invention, said host is a prokaryotic host selected from the group consisting of *E. coli, Bacillus* sp., *Pseudomonas* sp., *Streptomyces* sp., *Mycobacterium* sp., *Caulobacter* sp., *Rhodobacter* sp., *Lactococcus* sp., *Burkholderi* sp. and *Ralstonia* sp.

In another preferred embodiment of the present invention, said host expresses (a) the polypeptide encoded by the nucleic acid or polynucleotide of the present invention or the vector of the present invention.

THE FIGURES SHOW

FIG. 1A: Two-Domain Mechanism of Class B1 GPCR Binding and Activation: The extracellular N-domain of the GPCR binds with high affinity to the C-terminal part of the peptide ligand. This recruits the low-affinity, N-terminal effector part of the peptide ligand to the J-domain and induces a structural rearrangement of the transmembrane helices leading to intracellular signalling (e.g., G-protein activation).

FIG. 1B: Screening: A library of fragments linked to a short high-affinity peptide derived from the C-terminus of the native GPCR ligand is incubated with the GPCR. Through the strong peptide-N-domain interaction the local concentration of the tethered small molecules is dramatically increased in the vicinity of the J-domain of the GPCR. Those fragments with a weak affinity to the GPCR J-domain are identified by their effect on receptor function in cellular or biochemical assays. They then serve as starting points to develop compounds that can modulate GPCR function in absence of the peptide derived from the C-terminus of the native GPCR ligand.

FIG. 2A: Linked Peptides as Positive Controls: Covalent conjugates of the N-terminal activation domain from the CRF $R_1$ agonist rat urocortin ($Ucn_{1-19}$; SEQ ID, NO: 25) and a consensus peptide derived from the C-terminus of CRF $R_1$ antagonists (SEQ ID NO: 26) retain full CRF $R_1$ activation potency (testosterone production). Neither of the isolated domains is active alone[15].

FIG. 2B: High-affinity $CRF_1$ Peptide Antagonist: A minimal $CRF_{30-41}$ analog (SEQ ID NO: 27) binds tightly to the CRF1 receptor[16]. The essential amino acid residues, the C-terminal amide and the $E_1,K_4$-lactam bridge are underlined in bold (X=cyclohexylalanine). The arrow indicates a potential attachment site for small molecule fragments.

FIG. 2C: Attachment chemistry for Trans-Tethering: A library of small molecules (MW<250 Da) with a unique amine or thiol group is conjugated to activated high-affinity peptides. N-hydroxysuccinimide ester, bromoacetamido and 2-pyridyldithio groups are introduced by commercially available cross linkers. An aldehyde group can be generated by perjodate oxidation of corresponding diols. The relatively small carrier peptide allows fragment conjugation to be performed at high concentrations in organic solvents (1-10 mM). Subsequently, the conjugates are assayed in highly diluted aqueous buffers (100 nM).

Figure 3:
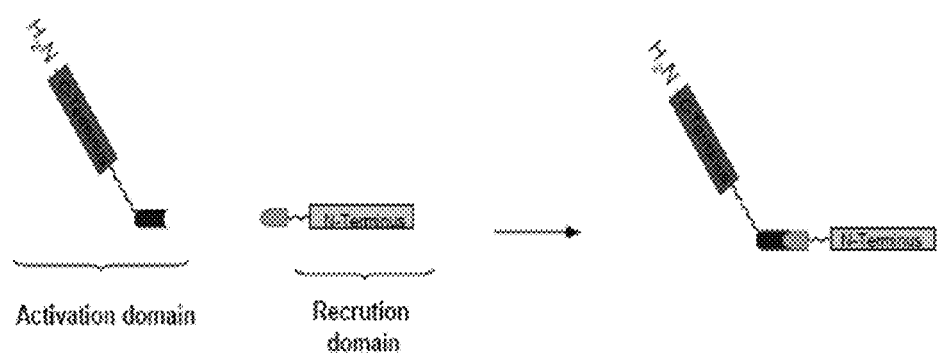

FIG. 3: Tethered Peptides: Coupling of peptidic activation and recrution domains by a bioconjugation reaction yield a full agonist in a straightforward manner. This strategy will allow the rapid synthesis of a library of peptide-peptide conjugates.

Figure 4:
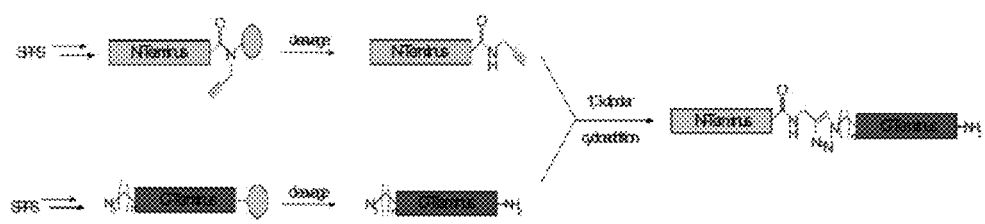

FIG. 4: Synthesis of the peptide-peptide conjugates: The peptidic fragments will be made by solid phase peptide synthesis. The biomimic conjugates will be coupled by "click-chemistry" reaction of a peptidic fragment containing an alkyne and a peptidic fragment containing an azide.

FIG. 5. Peptidic carrier and the N-terminal peptidic effector: (a) The peptide carrier will be chosen from the high affinity peptidic antagonist currently existing 1a and 2a. These antagonists will be modified to bear an azide group bound to the peptide by a spacer. (b) The synthesis of a peptide with a propargyl group appended to its carboxy terminal residue can be performed by using a terminal aldehyde based resin. Natural amino acid residues are given as their one-letter codes; X: L-cyclohexylalanine (Cha), B: L-Norleucine (Nle). The amino acid sequence comprised in compounds 1a and 1b is the sequence from position 2 to position 30 of SEQ ID NO: 2. The amino acid sequence comprised in compounds 2a and 2b is the sequence of SEQ ID NO: 27. The sequence shown in FIG. 5b is the sequence from position 1 to position 10 of SEQ ID NO: 9.

The following examples illustrate the invention but should not be construed as being limiting.

EXAMPLE 1

Screen for Small Organic Molecules (Fragments) Modulating the Human $CRF_1$ Receptor The 41aa neuropeptide Corticotropin-Releasing Factor (CRF) is the principal stress-response regulator in humans. The corresponding $CRF_1$ receptor has been validated as a prime target in behavioral disorders like anxiety and depression by transgenic mice, antisense approaches and small molecule intervention[13].

Beyermann et al. have shown that linking of isolated N- and C-terminal domains of CRF analogs, each inactive alone, reconstitutes full CRF agonism (FIG. 2A)[15]. More recently, Yamada et al. have developed a 12 amino acid analog of astressin that binds to the $CRF_1$ receptor with 5.5 nM affinity and is devoid of any detectable influence on the J-domain signaling (FIG. 2B)[16,17]. This peptide is coupled to commercially available fragments containing thiol or amine groups via established bioconjugation strategies (FIG. 2C). A modified effector domain of urocortin$_{1-19}$ is used as a positive control. Receptor activation by G protein-coupled cAMP production is used as read-out. Alternatively, fragments are tested for ligand-induced receptor internalization in a high-content screening, as recently shown for the CRF-antagonist astressin[17]. Enhancement of direct binding is assayed by competition with reporter peptides from $CRF_1$ membrane preparations. Similarly, allosteric inhibition is assayed by displacement of small molecule antagonists[18].

EXAMPLE 2

Screen for Peptides Modulating the Human $CRF_1$ Receptor

The synthesis of a library of CRF analogs is performed by tethering two peptidic fragments. These peptide-peptide conjugates are composed of a fixed C-terminal analog peptide with high affinity for the extracellular domain of CRFR and a variable N-terminal analog peptide designed to interact with the J-domain of the CRFR (FIG. 3).

The synthesis and coupling of short length peptides to form a full functional $CRFR_1$ modulator has several advantages with respect to the classical synthesis of the whole peptide (e.g. less time consuming higher product yields and purities). These advantages are exploited for the synthesis of modulators in a high-throughput fashion.

Conjugation Methodology.

The fragments are tethered by a one pot reaction of two functional groups compatible with most of the diverse functional groups present in peptides thus allowing the use of unprotected peptides. This can be achieved by "click-chemistry" reactions[1] (see FIG. 4). Specifically, the 1,3-dipolar cycloaddition of an azide and an alkyne that affords a triazol group under mild conditions is used.[2] The solid phase peptide synthesis (SPPS) of peptides containing a terminal alkyne group or an azide group and further "click-chemistry" reaction between the resulting fragments provides a library of peptide-peptide conjugates in a straightforward manner. Additionally, the introduction of an alkyne or azide group in a peptide is fully compatible with SPPS.[3] Alternatively, in case that a native amide bond is required, the attachment of fragments is performed by the Staudinger ligation[4], cysteine-free native chemical ligation[5] or ketoacid-isoxazolidine peptide formation.[6]

1 a) Kolb, H. C.; Finn, M. G.; Sharpless, K. B. *Angew. Chem. Int. Ed.* 2001, 40, 2004-2021.
b) Kolb, H. C.; Sharpless, K. B. *Drug Discovery Today* 2003, 8, 1128-1137.
2 a) Tornoe, C. W.; Christensen, C.; Meldal, M. *J. Org. Chem.* 2002, 67, 3057-3064.
b) Rostovtsev, V. V.; Green, L. G.; Fokin, V. V.; Sharpless, K. B. *Angew. Chem. Int. Ed.* 2002, 41, 2596-2599.
c) Pérez-Balderas, F.; Ortega-Muiñoz, M.; Morales-Sanfrutos, J.; Hernández-Mateo, F., Calvo-Flores, F. G.; Calvo-Asin, J. A.; Isac-Garcia, J.; Santoyo-González, F. *Org. Lett.* 2003, 5, 1951-1954.
3 a) Lin, H.; Walsh, C. T. *J. Am. Chem. Soc.* 2004, 126, 13998-14003.
b) Lundquist, J. T.; Pelletier, J. C. *Org. Lett.* 2001, 3, 781-783.
4 Köhn, M.; Breinbauer, R. *Angew. Chem. Int. Ed.* 2004, 43, 3106-3116.
5 Wu, B.; Chen, J.; Warren, J. D.; Chen, G.; Hua, Z.; Danishefsky, S. J. *Angew. Chem. Int. Ed.* 2006, 45, 4116-4125.
6 Carrillo, N.; Davalos, E. A; Russak, J. A; Bode, J. W. *J. Am. Chem. Soc.* 2006, 128, 1452-1453.

Selection of peptidic fragments for tethering: Peptidic carrier. The C-terminal peptidic carrier is chosen from the high affinity antagonist peptides existing in the literature such as astressin (1a)[6a] or the 12 aa analog (2a)[6b] (FIG. 5). Previous papers have shown that the chain elongation of a non-natural antagonist such as astressin can provide a full agonist with increased potency respect to CRF.[8d] The connection between both fragments is made through a linker.

Selection of Peptidic Fragments for Tethering:

N-terminal peptidic effector. It is well known that residues 4-8 of CRF play an important role in the activation[7] of CRFR.[8d] As initial N-terminal peptide the residues. 1-10 of h-CRF are used. This fragment is synthesized carrying a propargyl group appended to residue 10 (FIG. 5b). Synthesis of the compound shown in FIG. 5b is described in Example 6. Alternatively, the elongated or truncated of this N-terminal analog are used. These peptidic fragments serve as positive controls and as templates for the library design.

7 Rivier, J.; Spiess, J.; Vale, W. *Proc. Natl. Acad. Sci. USA* 1983, 80, 4851-4855.

Evaluation of the Activities.

The peptide-peptide conjugates of the initial N-terminal peptide and the different peptidic carrier are tested in order to confirm that these non-natural analogs retain the agonistic properties of hCRF and to choose the most appropriate carrier for this work. This evaluation consists in competitive receptor binding assays and as agonist by cAMP production assay.

Library Design.

A library of N-terminal fragments appended to a propargyl group is made by single point substitution of any residue of the control peptide previously identified (see above). First, by alteration of the side chain: At least one of each type of amino acids is introduced at each position. Second, by backbone modification: a natural amino acid is substituted by a peptoid or the respective β-amino acid. The influence of the N-backbone hydrogen bonding is investigated by systematic N-methylation. Third, by derivatization of the N-terminus: A broad range of commercially available capping groups is appended to the terminal amino group. This increases the diversity of the library and reduces the peptidic character.

The propargyl group reacts with an azide to yield a triazol which is one of the preferred linkers of the invention; see the synthesis of compound 9 in Example 6 below.

EXAMPLE 3

Ligands of Class B GPCRs and Truncated Forms Thereof Acting as Antagonists

Provided below is a compilation of ligands of class B GPCRs as well as of antagonists, together with reference to the pertinent literature. The sequences designated as antagonists are suitable second groups as well as building blocks of precursor compounds of in the invention. The ligands are exemplary reference compounds according to the invention. Sequences disclosed as SEQ ID NOS 4-8, 1, 9-13, 2-3, 14-16, 28-29, and 17-24, respectively, in order of appearance.

```
ANTAGONISTS
[Leu11, D-Trp12]PTHrP(7-34)
Nutt, R. F.; Caulfield, M. P.; Levy, J. J.;
Gibbons, S. W.; Rosenblatt, M.; McKee, R. L.
Endocrionlogy 127(1990)491-493.

[Ile5, Trp23, Tyr36]PTHrP (5-36)
Carter, P. H.; Juppner, H.; Gardella, T. J.
Endocrionology 140(1999)4972-4981.

SECRETIN RECEPTOR
HSDGTFTSELSRLREGARLQRLLQGLV-CONH2
Whitmore T. E., Holloway J. L., Lofton-Day C. E.,
Maurer M. F., Chen L., Quinton T. J., Vincent J.
B., Scherer S. W., Lok S. Cytogenet. Cell Genet.
90:47-52(2000).
```

CALCITONIN RECEPTOR and related

| | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| h-a-CGRP | | | | | | | A | C* | D | T | A | T | C* | V | T | H | R | L | A | G | L | L | S | R | S | G | G | V | V | K | N | N | F | V | P | T | N | V | G | S | K | A | - | F | CONH2 |
| h-b-CGRP | | | | | | | A | C* | N | T | A | T | C* | V | T | H | R | L | A | G | L | L | S | R | S | G | G | M | V | K | S | N | F | V | P | T | N | V | G | S | K | A | - | F | CONH2 |
| h-Amylin | | | | | | | K | C* | N | T | A | T | C* | A | T | Q | R | L | A | N | F | L | V | H | S | S | N | N | F | G | A | I | L | S | S | T | N | V | G | S | N | T | - | Y | CONH2 |
| h-Calciton | | | | | | | C* | G | N | L | S | T | C* | M | L | G | T | Y | T | Q | D | F | N | K | F | H | T | - | - | - | - | - | F | P | Q | T | A | I | G | V | G | A | - | P | CONH2 |
| Adrenomed. | Y | R | Q | S | M | N | N | F | Q | G | L | R | S | F | G | C* | R | F | G | T | C* | T | V | Q | K | L | A | H | Q | I | Y | Q | F | T | D | K | D | K | D | N | V | A | P | R | S | K | I | S | P | Q | G | Y | CONH2 | h-a-CGRP: Morris, H. R et al. Nature 308(1984)746-728.
h-b-CGRP: Steenbergh, P. H. et al. FEBS Letters 183(1985)403-407.
h-Amylin: Cooper, G. J. S. et al. Proc: Natl Acad. Sci. USA 84(1987)8628-8632.
h-Calciton: Neber, R. et al. Helvetica Chimica Acta 5 1(1968)1900-1905.
Adrenomedullin: Kitamura, K. et al. Biochemical and Biophysical Research communications 192(1993)553-560.

ANTAGONIST

| | | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| h-a-CGRP | | | | | | | | | | | | | | | | | | | | | | | | | | | | | | | | | | | | | F | V | P | T | D | V | G | P | F | A | - | F | CONH2 |

Rist, B.; Entzeroth, M.; Beck-Sickinger, A. G. J. Med. Chem. (41), 1988, 117-123.

CORTICOTROPIN RELEASING FACTOR RECEPTOR

| | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| h-CRP | S | E | E | P | P | I | S | L | D | L | T | F | H | L | L | R | E | V | L | E | M | A | R | A | E | Q | L | A | Q | Q | A | H | S | N | R | K | L | M | E | I | I | CONH2 |
| h-URP | - | - | - | I | V | L | S | L | D | V | P | I | G | L | L | Q | I | L | L | E | Q | A | R | A | R | A | A | R | E | Q | A | T | T | N | A | R | I | L | A | R | V | CONH2 |
| Svg | pE | G | P | P | I | S | I | D | L | S | L | E | L | L | R | K | M | I | E | I | E | K | Q | E | K | E | K | Q | Q | A | A | N | N | R | L | L | L | D | T | I | CONH2 |
| h-UCN I | D | N | P | S | L | S | I | D | L | T | F | H | L | L | P | T | L | L | E | L | A | R | T | Q | S | Q | R | E | R | A | E | Q | N | R | I | I | F | D | S | V | CONH2 |
| h-UCN III | | | F | T | L | S | L | D | V | P | T | N | I | M | N | L | L | F | N | I | A | K | A | K | N | L | R | A | Q | A | A | A | N | A | H | L | M | A | Q | I | CONH2 | h-CRF: Rivier et al. Proc. Natl. Acad. USA 80(1983)4851-4855.

```
ANTAGONISTS
fHLLREVLEBARAEQLAQE*AHK*NRKLBEII-CONH2
Gulyas, J et al. Proc. Natl. Acad. USA 92(1995)
10575-10579.

Ac-E*AEK*NRLXDII-CONH2
Yamada, Y. et al. J. Med. Chem. 47(2004)1075-1078.

PARATHYROID HORMONE RECEPTOR and related
PHT(1-84)  SVSEIQLMHNLGKHLNSMERVEWLRKKLQDVHNFVALGAP
LAPRDAGSQRPRKKEDNVLVESHEKSLGEADKADVDVLTKAKSQ
Keutman, H. T. et aL. Biochemistry 17(1978)5723-
5729.

PHT(1-34)  SVSEIQLMHNLGKHLNSMERVEWLRKKLQDVHNF
Brewer, H. B. et al. Proc. Natl. Acad. Sci. USA
69(1972)3585-3588.

TIP39  SLALAKKAAFRERARLLAALERRHWLNSYMHKLLVLDAP
Ustin, T. B. et al. Nature Neuroscience 2(1999)
941-943.

GLUCAGON RECEPTOR
Glucagon HSQGTFTSDYSKYLDSRRAQDFVQWLMNT
Thomsen J, Kristiansen K., Brunfeldt K., Sundby F.
FEBS Lett. 21:315-319(1972).

GLUCAGON-LIKE-PEPTIDE 1 RECEPTOR
Glucagon-like peptide 1 HAEGTFTSDVSSYLEGQAAKEFIAWL
VKGR
Mayo, K E et al. Pharmacological Reviews 55(2003)
167-194.

GLUCAGON-LIKE-PEPTIDE 2 RECEPTOR
Glucagon-like peptide 2 HADGSFSDEMNTILDNLAARDFINWL
IQTKITD
Mayo, K E et al. Pharmacological Reviews 55(2003)
167-194.

GIP RECEPTOR
GIP YAEGTFISDYSIAMDKIHQQDFVNWLLAQKGKKNDWKHNITQ
Mayo, K E et al. Pharmacological Reviews 55(2003)
167-194.
```

```
GROWTH HORMONE RELEASING HORMONE RECEPTOR
GHRH YADAIFTNSYRKVLGQLSARKLLQDIMSRQQGESNQERGARARL
Mayo, K E et al. Phannacological Reviews 55(2003)
167-194.

VPAC and VAC receptors
VIP HSDAVFTDNYTRLRKQMAVKKYLNSILN
UniProtKB/Swiss-Prot entry P01282

PACAP DVAHGILNEAYRKVLDQLSAGKHLQSLVARGVGGSLGGGAGDDA
EPLS
UniProtKB/Swiss-Prot entry P18509

Notes:
f = D-Phenyl alanine
pE = pyroglutamic acid
X = cyclohexyl alanine
B = NLeu
*Indicates an intramolecular cycle
Further antagonistic CRF-Analoga are described in:
  1. Hernandez, J. F., et at, Synthesis and
     relative potencies of new constrained CRF
     antagonists. J Med Chem, 1993. 36(20):
     p. 2860-7.
  2. Miranda, A., et al., Conformationally
     restricted competitive antagonists of human/
     rat corticotropin-releasing factor. J Med
     Chem, 1994. 37(10): p. 1450-9.
  3. Gulyas, J., et al., Potent, structurally
     constrained agonists and competitive antagon-
     ists of corticotropin-releasing factor. Proc
     Natl Acad Sci U S A, 1995. 92(23): p. 10575-9.
  4. Miranda, A., et al., Constrained cortico-
     tropin-releasing factor antagonists with i-
     (i + 3) Glu-Lys bridges. J Med Chem, 1997.
     40(22): p. 3651-3.
  5. Rivier, J., et al., Minimal-size, con-
     strained corticotropin-releasing factor
     agonists with i-(i + 3) Glu-Lys and Lys-Glu
     bridges. J Med Chem, 1998. 41(14): p. 2614-20.
  6. Rivier, J., et al., Astressin analogues (cor-
     ticotropin-releasing factor antagonists) with
     extended duration of action in the rat. J Med
     Chem, 1998. 41(25): p. 5012-9.
  7. Rivier, J. E., et al., Constrained corticotro-
     pin releasing factor antagonists (astressin
     analogues) with long duration of action in
     the rat. J Med Chem, 1999. 42(16): p. 3175-
     82.
  8. Rivier, J., et al., Potent and long-acting
     corticotropin releasing factor (CRF) receptor
     2 selective peptide competitive antagonists.
     J Med Chem, 2002. 45(21): p. 4737-47.
  9. Rijkers, D. T. S., et al., Structure-activity
     studies on the corticotropin releasing factor
     antagonist astressin, leading to a minimal
     sequence necessary for antagonistic activity.
     Chembiochem, 2004. 5(3): p. 340-8.
 10. Rijkers, D. T., J. A. den Hartog, and R. M.
     Liskanip, An optimized solid phase synthesis
     strategy--including on-resin lactamization--
     of astressin, its retro-, inverso-, and retro-
     inverso isomers as corticotropin releasing
     factor antagonists. Biopolymers, 2002. 63(2):
     p. 141-9.
 11. Rijkers, D. T., J. A. den Hartog, and R. M.
     Liskamp, Synthesis and biological activity of
     N-terminal lipidated and/or fluorescently
     labeled conjugates of astressin as corticotro-
     pin releasing factor antagonists. Bioorg Med
     Chem, 2004. 12(19): p. 5099-106.
 12. Yamada, Y., et al., New class of corticotro-
     pin-releasing factor (CRF) antagonists: small
     peptides having high binding affinity for CRF
     receptor. J Med Chem, 2004. 47(5): p. 1075-8.
as well as in:
EP1094072A1, WO01/29086A1
```

EXAMPLE 4

Linker Synthesis

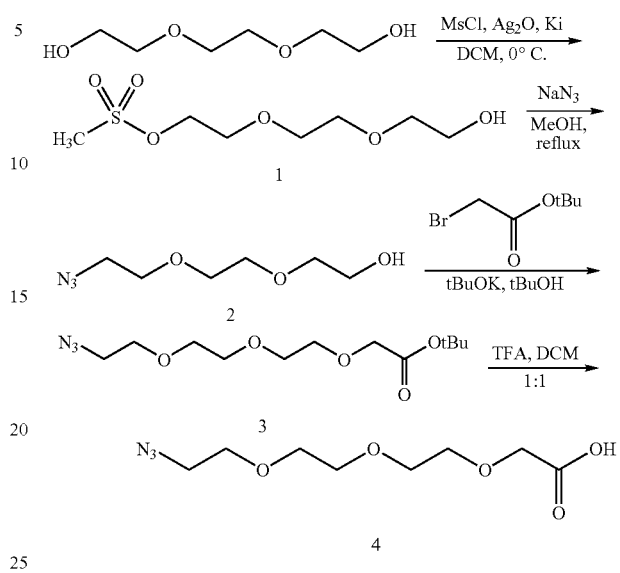

Compound 1

To a ice bath cooled solution of triethylene glycol (20 mmol) in 80 mL of dichloromethane were added 30 mmol of $Ag_2O$, 22 mmol of methanesulfonyl chloride and 0.4 mmol of potassium iodide. The reaction was stirred at 0° C. for 15 min, then filtered in a celite pad. The pad was washed with AcOEt and the solvent was evaporated under reduced pressure. The crude was purified by column chromatography (AcOEt) to yields 2.4 g (53%) of the desired product. The compound show $^1$H NMR data in complete concordance with those reported[8]

[8] Lebeau, L.; Oudet, P.; Mioskowski, C. *Helv. Chim. Acta* 1991, 74, 1697-1706.

Compound 2

10.4 mmol of sodium azide were added to a solution of 5.2 mmol of 1 in 20 mL of methanol. The solution was stirred at reflux for 16 h. The reaction was cooled to rt, filtered and concentrated at vacuum. The crude was purified by column chromatography (AcOEt:hexane 2:1) to yields 0.68 g (75%) of the desired product. The compound show $^1$H NMR data in complete concordance with those reported[9].

[9] Rensen, P. C. N.; van Leeuwen, S. H.; Sliedregt, L. A. J. M; van Berkel, T. J. C.; Biessen, E. A. L. *J. Med. Chem.* 2004, 47, 5798-5808.

Compound 3

To a solution of 1.42 mmol of 3 in 10 mL of 2-methyl-2-propanol was added 2.1 mmol of potassium tert-butoxide. The solution was stirred at 30° C. for 15 min and then 1.7 mmol of tert-butyl bromoacetate were added. After 5 h at 30° C. additional potassium tert-butoxide (0.4 mmol) and tert-butyl bromoacetate (0.71 mmol) were added and the reaction was stirred at 30° C. for additional 16 h. The solvent was evaporated under vacuum, the crude was redisolved in 25 mL of dichloromethane and washed with water (25 mL) the aqueous layer was washed 3 times with dichloromethane. The organic fractions were collected and washed twice with water. The organic layer was dried ($MgSO_4$) and evaporated under reduced pressure. Column chromatography (AcOEt/hexane 1:2) yields 405 mg (99%) of the desired compound as a yellow oil: $^1$H NMR (400 MHz, $CDCl_3$): δ 3.99 (s, 2H), 3.70-3.63 (m, 10H), 3.36 (t, 2H, J=5.3 Hz), 1.44 (s, 9H); $^{13}$C NMR (100 MHz, $CDCl_3$): δ 169.9, 81.7, 70.9, 70.9, 70.9, 70.9, 70.2, 69.3, 50.9, 28.3.

Compound 4

To a solution of 380 mg of 3 in 10 mL of dichloromethane was added 10 mL of trifluoroacetic acid, the solution was stirred at rt for 2 h. The solvent was evaporated, the crude was redisolved in 5 mL of water and the pH was adjusted to 10 by addition of 1 M NaOH, the aqueous layer was washed twice with dichloromethane and then the pH was adjusted to 3 by addition of HCl 10%. The product was extracted 15 times with 15 mL of AcOEt, dried (MgSO$_4$) and evaporated to yields 275 mg (90%) of product as yellow oil: $^1$H NMR (400 MHz, CDCl$_3$): δ 7.10 (bs, 1H), 4.04 (t, 2H), 3.9-3.6 (m, 10H), 3.51 (t, 2H); $^{13}$C NMR (100 MHz, CDCl$_3$): δ 169.9, 81.7, 70.9, 70.9, 70.9, 70.9, 70.2, 69.3, 50.9, 28.3.

EXAMPLE 5

Synthesis of a Peptide Linked to Reactive Group

Compound 5 (SEQ ID NO: 30)

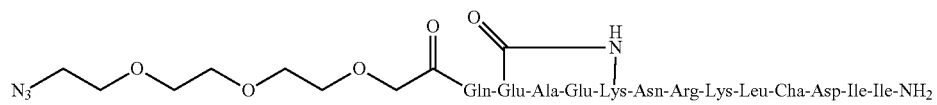

5

Rink amide resin (Novabiochem, 100-200 mesh, 0.59 mmol/g resin) (44 mg, 0.026 mmol) was loaded in a 5 mL MultiSynTech Reaktor (MultiSynTech GmbH), pre-swollen in dichloromethane for 1 h. The resin was filtered and washed with DMF (1 mL×4). Attachment of the first amino acid: The resin was treated with 20% of 4-methylpiperidine in DMF (1 mL) for 20 min and washed with DMF (1 mL×4). A solution of Fmoc-Ile-OH (46 mg, 0.13 mmol), HATU (49 mg, 0.13 mmol) and DIPA (46 μL, 0.26 mmol) in 1 mL of NMP was added and the resin was shaked for 4 h until chloranil test negative. The resin was filtered and washed with DMF (1 mL×4), treated with 1% of acetic anhydride and 2% of DIPA in NMP (1 mL) for 15 min and washed with DMF (1 mL×4). Elongation of the peptidic chain: The resin was treated with 20% of 4-methylpiperidine in DMF (1 mL) for 20 min and washed with DMF (1 mL×4). A solution of Fmoc-Ile-OH (46 mg, 0.13 mmol), HBTU (49 mg, 0.13 mmol), HOBt (18 mg, 0.13 mmol) and DIPA (46 μL, 0.26 mmol) in 1 mL of NMP was added and the resin was shaked for 1 h 15 min until kaiser test negative. The resin was filtered and washed with DMF (1 mL×4), treated with 1% of acetic anhydride and 2% of DIPA in NMP (1 mL) for 15 min and washed with DMF (1 mL×4). The above elongation procedure was repeated with Fmoc-Asp(OtBu)-OH (53 mg, 1 h), Fmoc-Cha-OH (1 h 35 min), Fmoc-Leu-OH (1 h 15 min), Fmoc-Lys(Boc)-OH (1 h 15 min), Fmoc-Arg(Pbf)-OH (1 h 30 min), Fmoc-Asn(Trt)-OH (2 h 30 min), Fmoc-Lys(Aloc)-OH (1 h 30 min), Fmoc-Glu(tBu)-OH (2 h), Fmoc-Ala-OH (1 h 40 min) and Fmoc-Glu(allyl esther)-OH (1 h 45 min). The resin was treated with 1% 4-methylpiperidine in DMF (1 mL) for 20 min, washed with DMF (1 mL×4), treated with Fmoc-Gln(Trt)-OH (79.4 mg, 0.13 mmol) for 2 h and washed with DMF (1 mL×4). A solution of 1% of acetic acid and 2% DIPA in NMP (1 mL) was added to the resin and shaked for 15 min, washed with DMF (1 mL×4), methanol (1 mL×2), dichloromethane (1 mL×4), and diethylether (1 mL) and dried under vacuum overnight. The resin was transferred to a reaction tube and 2 mL of CHCl$_3$/acetic acid/NMM 92.5:5:2.5 were added. Argon gas was bubbled for 15 min and then Pd(PPh$_3$)$_4$ (90 mg, 0.078 mmol) was added, the reaction was shaked for 16 h. After this time the resin was transferred to a Multisyntek Reaktor and washed with chloroform (1 mL×4), DMF (1 mL×3), 0.5% of DIPA in DMF (1 mL×3), 0.02 M Et$_2$NCS$_2$Na in DMF (1 mL×3×20 min) and DMF (1 mL×4). A solution of PyBoP (36 mg, 0.07 mmol) was added to the resin and shaked for 16 h until kaiser test negative. The resin was filtered and washed with DMF (1 mL×4). The terminal Fmoc group was released by treatment with 20% of 4-methylpiperidine in DMF (1 mL) for 20 min, The resin was washed with DMF (1 mL×4) and treated with a solution of 4 (24 mg, 0.104 mmol), HBTU (40 mg, 0.104 mmol), HOBt (14 mg, 0.104 mmol) and DIPA (37 mL, 0.208 mmol) in NMP (1 mL) for 2 h. The resin was transferred into a vial, treated with 1 mL of TFA/DMB/TIS (92.5:5:2.5) for 2 h, filtered and washed with TFA (0.5 mL×2). To this solution 50 mL of cold diethylether/hexane 1:1 were added and centrifugation precipitated a solid that was washed with diethylether/hexane 1:1. The purification of this product was made as follows: The crude was dissolved in 2 mL of water/acetonitrile/TFA 80:20:0.1 and loaded onto the column (Phenomenex Jupiter 10u Proteo 90A 250×21.2 mm) at a flow rate of 25 mL/min. The mobile phase was held at buffer A (0.1% TFA in acetonitrile/water 5:95) for 4 min, then the gradient started from 0% of B (0.1% TFA in acetonitrile/water 95:5) in A to 52% of B in A for 16 min. The fractions containing the peptide were lyophilized to yield 6.2 mg (13%) of white solid: HRMS (m/z) (MALDI-TOF) calc. for C$_{79}$H$_{135}$N$_{24}$O$_{24}$ [M+H]$^+$: 1806.024. found 1806.025.

EXAMPLE 6

Synthesis of a Test Compound

Compound 6

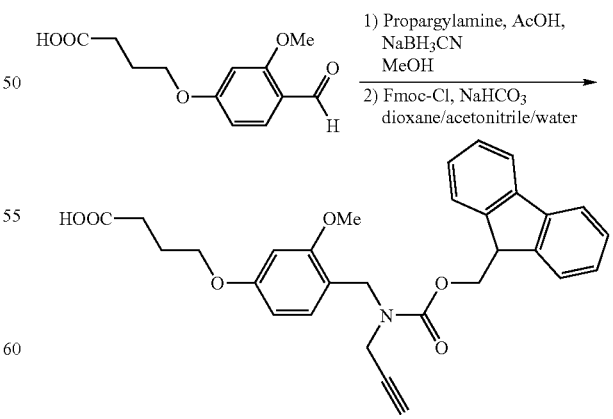

To a solution of 4-(4-formyl-3-methoxy-phenoxy)-butyric acid (100 mg, 0.42 mmol) in 5 mL of methanol were added propargylamine (47 mg, 0.84 mmol) and acetic acid (50 mg, 0.84 mmol). The solution was stirred at rt for 5 min and then solid NaBH$_3$CN (32 mg, 0.5 mmol) was added. The reaction was stirred at rt for 1 h 30 min. The solvent was evaporated, the crude was redissolved in 4 mL of acetonitrile/water 1:1 and solid NaHCO$_3$ was added (176 mg, 2.1 mmol). This stirred solution was cooled in a ice bath for 10 min and a solution of 9H-fluoren-9-ylmethyl chloridocarbonate (300 mg, 1.05 mmol) was added. The reaction was kept at 0° C. for 1 h 30 min and then at rt for 16 h. The pH of the solution was adjusted to 3 by addition of 10% HCl, the organic solvent was evaporated and the aqueous layer was washed twice with AcOEt. The organic fractions were collected, dried (MgSO$_4$) and evaporated under vacuum. The crude was purified by column chromatography (AcOEt:hexane 1:1→2:1) yielding 163 mg (78%) of 6 as white amorphous solid: $^1$H NMR (400 MHz, CDCl$_3$): δ 7.75 (d, 2H, J=7.3 Hz), 7.67 (d, 1H, J=6.3 Hz), 7.52 (d, 1H. J=6.4 Hz), 7.39 (t, 2H, J=7.3 Hz), 7.34-7.12 (m, 2H), 6.86 (d, 1H, J=7.4 Hz), 6.5-6.3 (m, 2H), 4.6-4.4 (m, 4H), 4.3-4.2 (m, 1H), 4.1-4.0 (m, 4H), 3.79 (s, 3H), 2.60 (t, 2H, J=7.3 Hz), 2.22 (bs, 1H), 2.13 (t, 2H, J=6.9 Hz).
Resin 7

Compound 8 (residues 1-10 of SEQ ID NO: 9)

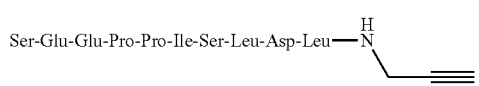

Attachment of the first amino acid: The resin 7 was loaded in a 5 mL MultiSynTech Reaktor (MultiSynTech GmbH), pre-swollen in dichloromethane for 1 h, washed with DMF (3 mL×3) and treated with a solution of 20% of 4-methylpiperidine in DMF (3 mL) for 15 min. The resin was washed with DMF (3 mL×4) and to the resin a solution of Fmoc-Leu-OH (152 mg, 0.43 mmol), HATU (164 mg, 0.43 mmol) and DIPA (151 µL, 0.86 mmol) were added. The mixture was shaked for 2 h until chloranil test negative. The resin was washed with DMF (3 mL×3), treated with 1% of acetic acid, 2% of DIPA in NMP (3 mL) for 15 min and washed with DMF (3 mL×3). Elongation of the peptidic chain: the resin was treated with a solution of 20% of 4-methylpiperidine in DMF (3 mL) for 20 min, washed with DMF (3 mL×4), treated with a solution of

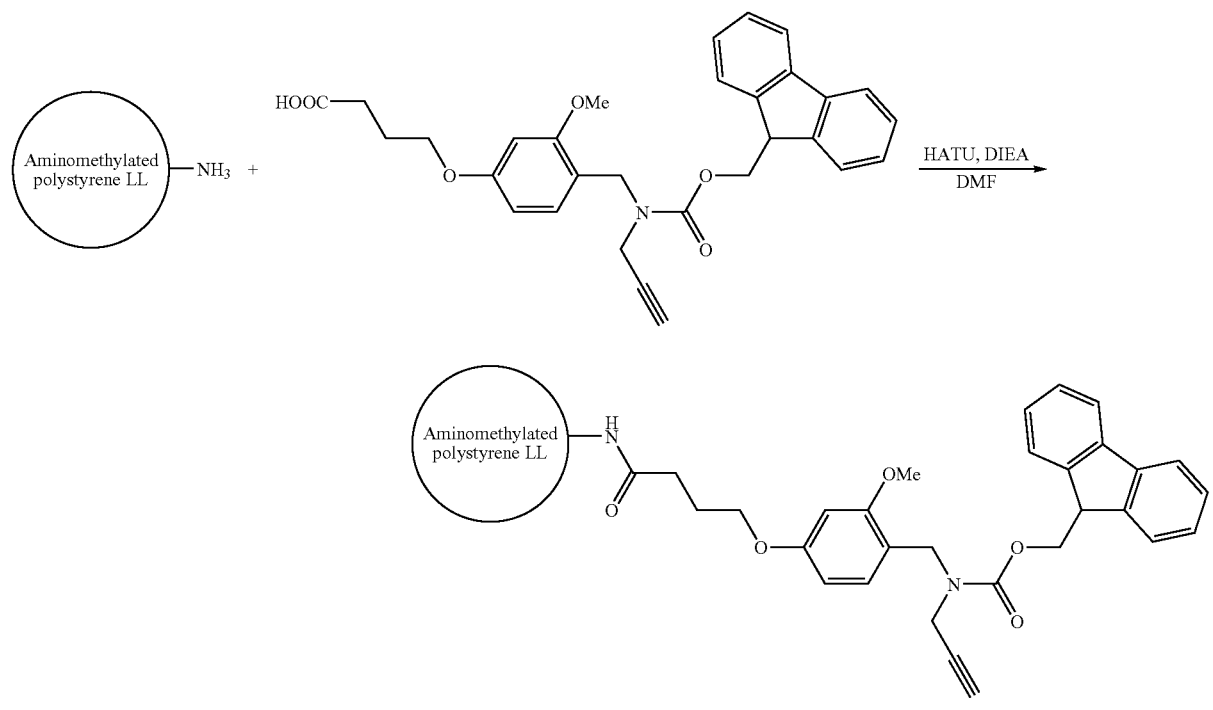

Aminomethylated polystyrene LL (Novabiochem, 100-200 mesh, 0.46 mmol/g resin) (230 mg, 0.11 mmol) was loaded in a 5 mL MultiSynTech Reaktor (MultiSynTech GmbH), pre-swollen in dichloromethane for 1 h and washed with DMF (3 mL×3). A solution of 6 (200 mg, 0.43 mmol), HATU (164 mg, 0.43 mmol) and DIPA (151 µL, 0.86 mmol) in DMF (3 mL) was added to the resin, the resin was shaked for 6 h until kaiser test negative and washed with DMF (3 mL×3). The resin was treated with 1% of acetic acid and 2% of DIPA in DMF (3 mL) for 15 min, washed with DMF (3 mL×4), methanol (3 mL×2), dichloromethane (3 mL×4), diethylether (3 mL) and dried.

Fmoc-Asp(OtBu)-OH (177 mg, 0.43 mmol), HBTU (163 mg, 0.43 mmol), HOBt (58 mg, 0.43 mmol) and DIPA (151 mL, 0.86 mmol) in NMP (3 mL) for 2 h until kaiser test negative and washed with DMF (3 mL×3). The resin was then treated with 1% of acetic acid and 2% of DIPA in NMP (3 mL) for 15 min and washed with DMF (3 mL×3). The above elongation procedure was repeated with Fmoc-Leu-OH (152 mg, 1 h 45 min), Fmoc-Ser(tBu)-OH (165 mg, 1 h), Fmoc-Ile-OH (152 mg, 1 h 30 min), Fmoc-Pro-OH (145 mg, 1 h 45 min), Fmoc-Pro-OH (145 mg, 1 h 10 min) by using HATU coupling procedure, Fmoc-Glu(OtBu)-OH (183 mg, 1 h 30 min) by using HATU coupling procedure, Fmoc-Glu(OtBu)-OH (183 mg, 1 h 10 min) and Fmoc-Ser(tBu)-OH (165 mg, 2 h). Finally the resin was treated with 20% of 4-methylpiperidine in DMF (3 mL) for 20 min to deprotect the terminal amine group, washed with DMF (3 mL×4), methanol (3 mL×2), dichloromethane (3 mL×4), diethylether (3 mL) and dried under vacuum overnight. The resin was transferred into a vial, treated with 3 mL of TFA/TIS/water (95:2.5:2.5) for 2 h, filtered and washed with TFA (0.5 mL×2). To the solution 50 mL of cold diethylether/hexane 1:1 and centrifugation precipitated a solid that was washed with diethylether/hexane 1:1. The purification of this product was made as follows: The crude was dissolved in 2 mL of water/acetonitrile/TFA-80:20:0.1 and loaded onto the column (Phenomenex Jupiter 10u Proteo 90A 250×21.2 mm) at a flow rate of 25 mL/min. The movile phase was held at buffer A (0.1% TFA in acetonitrile/water 5:95) for 4 min, then the gradient started from 0% of B (0.1% TFA in acetonitrile/water 95:5) in A to 30% of B in A for 3 min and from 30% of B in A to 40% of B in A for 15 min. The fractions containing the peptide were lyophilized to yield 45. 5 mg (38%) of pure peptide as white amorphous powder: HRMS (m/z). (MALDI-TOF) calc. for $C_{59}H_{82}N_{11}O_{18}$ [M+H]$^+$: 1136.584. found 1136.582.

Compound 9 (Drawing Discloses Residues 1-10 of SEQ ID NO: 9, SEQ ID NO: 30, Residues 1-10 of SEQ ID NO: 9, and SEQ ID NO: 30, Respectively, in Order of Appearance)

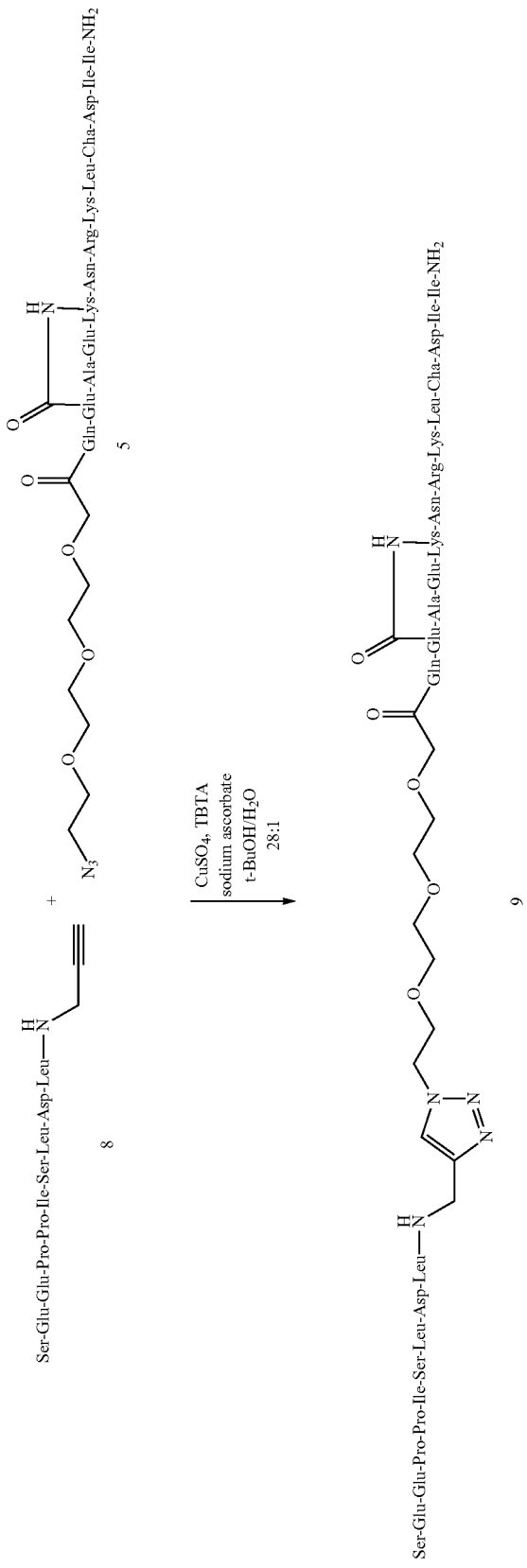

To a solution of 5 (100 nmol), 8 (300 nmol), CuSO$_4$ (12 nmol) and TBTA (12 nmol) in 290 μL of tert-butanol and 9 μL of water a solution of sodium ascorbate (30 nmol) in 1 μL of water were added. The reaction was shaked for 19 h at 37° C. until complete compsumition of compound 5. The purification of this product was made as follows: The crude was dissolved in 46 μL of water/acetonitrile/TFA 80:20:0.1 and 21 μL were loaded onto the column (Phenomenex Jupiter 4u Proteo 90A 250×4.6 mm) at a flow rate of 1 mL/min. The movile phase was held at buffer A (0.1% TFA in acetonitrile/water 5:95) for 4 min, then the gradient started from 0% of B (0.1% TFA in acetonitrile/water 95:5) in A to 52% of B in A for 16 min. The fractions containing the peptide were lyophilized to yields the desired product: MS (m/z) (MALDI-TOF) calc. for $C_{138}H_{216}N_{35}O_{42}$ [M+H]$^+$: 3035.6. found 3035.6.

ABBREVIATIONS

AcOEt: Ethylacetate; Cha: Cyclohexylalanine; DIPA: Diisopropylamine; DMB: 1,3-Dimethoxybenzene; DMF: N,N-Dimethylformamide; Fmoc: 9H-Fluoren-9-ylmethyl carbonate; HATU: O-(7-Azabenzotriazol-1-yl)-N,N,N',N'-tetramethyluronium hexafluorophosphate; HBTU: O-(Benzotriazol-1-yl)-N,N,N',N'-tetramethyluronium hexafluorophosphate; HOBt: 1-Hydroxybenzotriazole hydrate; HRMS: High resolution mass spectroscopy; MALDI-TOF: Matrix-assisted laser desorption/ionization-time of flight; NMM: N-methylmorpholine; NMP: N-methylpyrrolidone; NMR: Nuclear magnetic resonance spectroscopy; PyBoP: (Benzotriazol-1-yloxy)tripyrrolidinophosphonium hexafluorophosphate; TBTA: Tris[(1-benzyl-1H-1,2,3-triazol-4-yl)methyl] amine; TFA: Trifluoroacetic acid; TIS: Triisopropylsilane

FURTHER REFERENCES

The references cited in Examples 2 and 3 are provided as footnotes with a distinct numbering scheme in each Example. The remainder of the references, to the extent it is not directly incorporated into the text, is compiled below.

1) S. R. Hoare, Drug Discov. Today (2005), 10, 417-427.
2) A. J. Harmar, Genome Biol. (2001), 23, 3013.1-3013.10.
3) J. Saunders, Bioorg. Med. Chem. Lett. (2005), 15, 3653.
4) E. R Zartler, M. J. Shapiro, Curr. Opin. Chem. Biol. (2005), 9, 366-370.
5) R. A. Carr, M. Congreve, C. W. Murray, D. C. Rees, Drug. Discov. Today (2005), 10, 987-992.
6) D. A. Erlanson, R. S. McDowell, T. O'Brien, J. Med. Chem. (2004), 47, 3463-3482;
7) R. S. Bohacek, C. McMartin, W. C. Guida, Med. Res. Rev. (1996), 16, 3-50.
8) M. M. Hann, A. R. Leach, G. Harper, J. Chem. Inf. Comput. Sci. (2001), 41, 856-864.
9) A. L. Hopkins, C. R. Groom, A. Alex, Drug Discov. Today (2004), 9, 430-431.
10) D. A. Erlanson et al., Proc. Natl. Acad. Sci. U S A (2000), 97, 9367-9372.
11) E. Buck, J. A. Wells, Proc. Natl. Acad. Sci. U S A (2005), 102, 2719-2724.
12) S. R. Hoare et al., Biochemistry (2004), 43, 3996-4011.
13) J. M. H. M. Reul, F. Holsboer, Curr. Opin. Pharmacol. (2002), 2, 23-33.
14) D. E. Grigoriadis, Expert Opin. Ther. Targets (2005), 9, 651-684.
15) M. Beyermann et al., J. Biol. Chem. (2000), 275, 5702-5709.
16) Y. Yamada et al., J. Med. Chem. (2004), 47, 1075-1078.
17) S. J. Perry et al., J. Biol. Chem. (2005), 280, 11560-11568.
18) S. R. Hoare, S. K. Sullivan, N. Ling, P. D. Crowe, D. E. Grigoriadis, Mol. Pharmacol. (2003), 63, 751-765.

The invention claimed is:

1. A method of identifying a compound capable of forming a weak bond with a target domain of a G-protein coupled receptor comprising the steps of:
   (a) providing a receptor comprising said target domain and a first group linked to said target domain, wherein said target domain comprises the transmembrane or juxtamembrane domain of said G-protein coupled receptor, and wherein said first group comprises:
      (i) the N-terminal domain of said G-protein coupled receptor;
      (ii) the N-terminal domain of a different G-protein coupled receptor fragment or analog thereof; or
      (iii) avidin or biotin; a metal ion or chelator; a strep-tag or strep-tactin; glutathion or GST; tetracystein or diarsen;
   (b) bringing into contact said receptor of (a) with a test molecule comprising a second group and said compound linked to each other, wherein said first group binds said second group, wherein said second group comprises a component selected from the group consisting of
      (i) the C-terminal part of a natural cognate ligand of said G-protein coupled receptor defined in (a) (i) or (ii) capable of binding said N-terminal domain defined in (a) (i) or (ii); and
      (ii) biotin or avidin; a metal ion or chelator; a strep-tag or strep-tactin; glutathion or GST; tetracystein or diarsen; and
   (c) determining, subsequent to the binding of said first group to said second group, whether said compound forms a weak bond to said target domain,
   and wherein said compound is a peptide, peptidomimetic or small organic molecule, thereby identifying a compound capable of forming a weak bond with a target domain of a G-protein coupled receptor.

2. The method of claim 1, wherein said first group is linked to at least one of the N-Terminus of said transmembrane domain, the N-terminus of said juxtamembrane domain.

3. The method of claim 1, wherein said G-protein coupled receptor is a class B G-protein coupled receptor.

4. The method of claim 3, wherein said class B G-protein coupled receptor is selected from the group consisting of corticotropin releasing factor receptors CRFR1, CRFR2a, CRFR2b and CRFR2c; parathyroid hormone receptors PTHR1 and PTHR2; glucagon receptor; growth hormone releasing hormone receptor; glucagon-related peptide receptors GLP 1 R and GLP2R; gastric inhibitory polypeptide receptor; secretin receptor; calcitonin receptor; calcitonin receptor-like receptor; vasoactive intestinal peptide receptors VIPR1 and VIPR2; and adenylate cyclase activating polypeptide 1 receptor.

5. The method of claim 1, wherein said compound is selected from the group consisting of a peptide, a peptidomimetic and a small organic molecule.

6. The method of claim 1, wherein said compound has a molecular weight below 300 Da.

7. The method of claim 1, wherein said receptor is selected from the group consisting of
   (i) solubilized; and
   (ii) located in a membrane of a micelle or a membrane preparation.

8. The method of claim 1, wherein said target domain and said first group, and/or wherein said second group and said compound are linked through a linker, said linker is selected from the group consisting of alkyl with 1 to 30 carbon atoms, polyethylene glycol with 1 to 20 ethylene moieties, polyalanine with 1 to 20 residues, caproic acid, substituted or unsubstituted poly-p-phenylene and triazol.

* * * * *

SEQUENCE LISTING

```
<160> NUMBER OF SEQ ID NOS: 30

<210> SEQ ID NO 1
<211> LENGTH: 11
<212> TYPE: PRT
<213> ORGANISM: Homo sapiens

<400> SEQUENCE: 1

Phe Val Pro Thr Asp Val Gly Pro Phe Ala Phe
1               5                   10

<210> SEQ ID NO 2
<211> LENGTH: 30
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (10)..(10)
<223> OTHER INFORMATION: NLeu
<220> FEATURE:
<221> NAME/KEY: MISC_FEATURE
<222> LOCATION: (19)..(22)
<223> OTHER INFORMATION: Side chain-side peptide bond
<220> FEATURE:
<221> NAME/KEY: MOD_RES
<222> LOCATION: (27)..(27)
```

```
<223> OTHER INFORMATION: NLeu

<400> SEQUENCE: 2

Phe His Leu Leu Arg Glu Val Leu Glu Leu Ala Arg Ala Glu Gln Leu
1               5                   10                  15

Ala Gln Glu Ala His Lys Asn Arg Lys Leu Leu Glu Ile Ile
            20                  25                  30

<210> SEQ ID NO 3
<211> LENGTH: 11
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Side chain-side peptide bond
<220> FEATURE:
<221> NAME/KEY: MOD_RES
<222> LOCATION: (8)..(8)
<223> OTHER INFORMATION: Cyclohexylalanine

<400> SEQUENCE: 3

Glu Ala Glu Lys Asn Arg Leu Ala Asp Ile Ile
1               5                   10

<210> SEQ ID NO 4
<211> LENGTH: 37
<212> TYPE: PRT
<213> ORGANISM: Homo sapiens
<220> FEATURE:
<221> NAME/KEY: MISC_FEATURE
<222> LOCATION: (2)..(7)
<223> OTHER INFORMATION: Disulfide bridge

<400> SEQUENCE: 4

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 5
<211> LENGTH: 37
<212> TYPE: PRT
<213> ORGANISM: Homo sapiens
<220> FEATURE:
<221> NAME/KEY: MISC_FEATURE
<222> LOCATION: (2)..(7)
<223> OTHER INFORMATION: Disulfide bridge

<400> SEQUENCE: 5

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 6
<211> LENGTH: 37
<212> TYPE: PRT
<213> ORGANISM: Homo sapiens
<220> FEATURE:
<221> NAME/KEY: MISC_FEATURE
<222> LOCATION: (2)..(7)
<223> OTHER INFORMATION: Disulfide bridge
```

```
<400> SEQUENCE: 6

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Thr Asn Val
            20                  25                  30

Gly Ser Asn Thr Tyr
            35

<210> SEQ ID NO 7
<211> LENGTH: 32
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: Disulfide bridge

<400> SEQUENCE: 7

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 8
<211> LENGTH: 52
<212> TYPE: PRT
<213> ORGANISM: Homo sapiens
<220> FEATURE:
<221> NAME/KEY: MISC_FEATURE
<222> LOCATION: (16)..(21)
<223> OTHER INFORMATION: Disulfide bridge

<400> SEQUENCE: 8

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 9
<211> LENGTH: 41
<212> TYPE: PRT
<213> ORGANISM: Homo sapiens

<400> SEQUENCE: 9

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 10
<211> LENGTH: 38
<212> TYPE: PRT
<213> ORGANISM: Homo sapiens

<400> SEQUENCE: 10

Ile Val Leu Ser Leu Asp Val Pro Ile Gly Leu Leu Gln Ile Leu Leu
```

```
                1               5                  10                  15
Glu Gln Ala Arg Ala Arg Ala Ala Arg Glu Gln Ala Thr Thr Asn Ala
                        20                  25                  30

Arg Ile Leu Ala Arg Val
            35

<210> SEQ ID NO 11
<211> LENGTH: 40
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Pyroglutamic acid

<400> SEQUENCE: 11

Glu Gly Pro Pro Ile Ser Ile Asp Leu Ser Leu Glu Leu Leu Arg Lys
1               5                  10                  15

Met Ile Glu Ile Glu Lys Gln Glu Lys Glu Lys Gln Gln Ala Ala Asn
                20                  25                  30

Asn Arg Leu Leu Leu Asp Thr Ile
            35                  40

<210> SEQ ID NO 12
<211> LENGTH: 40
<212> TYPE: PRT
<213> ORGANISM: Homo sapiens

<400> SEQUENCE: 12

Asp Asn Pro Ser Leu Ser Ile Asp Leu Thr Phe His Leu Leu Pro Thr
1               5                  10                  15

Leu Leu Glu Leu Ala Arg Thr Gln Ser Gln Arg Glu Arg Ala Glu Gln
                20                  25                  30

Asn Arg Ile Ile Phe Asp Ser Val
            35                  40

<210> SEQ ID NO 13
<211> LENGTH: 38
<212> TYPE: PRT
<213> ORGANISM: Homo sapiens

<400> SEQUENCE: 13

Phe Thr Leu Ser Leu Asp Val Pro Thr Asn Ile Met Asn Leu Leu Phe
1               5                  10                  15

Asn Ile Ala Lys Ala Lys Asn Leu Arg Ala Gln Ala Ala Ala Asn Ala
                20                  25                  30

His Leu Met Ala Gln Ile
            35

<210> SEQ ID NO 14
<211> LENGTH: 84
<212> TYPE: PRT
<213> ORGANISM: Homo sapiens

<400> SEQUENCE: 14

Ser Val Ser Glu Ile Gln Leu Met His Asn Leu Gly Lys His Leu Asn
1               5                  10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45
```

-continued

Gln Arg Pro Arg Lys Lys Glu Asp Asn Val Leu Val Glu Ser His Glu
            50                  55                  60

Lys Ser Leu Gly Glu Ala Asp Lys Ala Asp Val Asp Val Leu Thr Lys
 65                  70                  75                  80

Ala Lys Ser Gln

<210> SEQ ID NO 15
<211> LENGTH: 34
<212> TYPE: PRT
<213> ORGANISM: Homo sapiens

<400> SEQUENCE: 15

Ser Val Ser Glu Ile Gln Leu Met His Asn Leu Gly Lys His Leu Asn
  1               5                  10                  15

Ser Met Glu Arg Val Glu Trp Leu Arg Lys Lys Leu Gln Asp Val His
             20                  25                  30

Asn Phe

<210> SEQ ID NO 16
<211> LENGTH: 39
<212> TYPE: PRT
<213> ORGANISM: Homo sapiens

<400> SEQUENCE: 16

Ser Leu Ala Leu Ala Lys Lys Ala Ala Phe Arg Glu Arg Ala Arg Leu
  1               5                  10                  15

Leu Ala Leu Glu Arg Arg His Trp Leu Asn Ser Tyr Met His Lys
             20                  25                  30

Leu Leu Val Leu Asp Ala Pro
         35

<210> SEQ ID NO 17
<211> LENGTH: 27
<212> TYPE: PRT
<213> ORGANISM: Homo sapiens

<400> SEQUENCE: 17

His Ser Asp Gly Thr Phe Thr Ser Glu Leu Ser Arg Leu Arg Glu Gly
  1               5                  10                  15

Ala Arg Leu Gln Arg Leu Leu Gln Gly Leu Val
             20                  25

<210> SEQ ID NO 18
<211> LENGTH: 29
<212> TYPE: PRT
<213> ORGANISM: Homo sapiens

<400> SEQUENCE: 18

His Ser Gln Gly Thr Phe Thr Ser Asp Tyr Ser Lys Tyr Leu Asp Ser
  1               5                  10                  15

Arg Arg Ala Gln Asp Phe Val Gln Trp Leu Met Asn Thr
             20                  25

<210> SEQ ID NO 19
<211> LENGTH: 30
<212> TYPE: PRT
<213> ORGANISM: Homo sapiens

<400> SEQUENCE: 19

His Ala Glu Gly Thr Phe Thr Ser Asp Val Ser Ser Tyr Leu Glu Gly
  1               5                  10                  15

```
Gln Ala Ala Lys Glu Phe Ile Ala Trp Leu Val Lys Gly Arg
         20                  25                  30

<210> SEQ ID NO 20
<211> LENGTH: 33
<212> TYPE: PRT
<213> ORGANISM: Homo sapiens

<400> SEQUENCE: 20

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 21
<211> LENGTH: 42
<212> TYPE: PRT
<213> ORGANISM: Homo sapiens

<400> SEQUENCE: 21

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 22
<211> LENGTH: 44
<212> TYPE: PRT
<213> ORGANISM: Homo sapiens

<400> SEQUENCE: 22

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
            35                  40

<210> SEQ ID NO 23
<211> LENGTH: 28
<212> TYPE: PRT
<213> ORGANISM: Homo sapiens

<400> SEQUENCE: 23

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 24
<211> LENGTH: 48
<212> TYPE: PRT
<213> ORGANISM: Homo sapiens

<400> SEQUENCE: 24

Asp Val Ala His Gly Ile Leu Asn Glu Ala Tyr Arg Lys Val Leu Asp
1               5                   10                  15

Gln Leu Ser Ala Gly Lys His Leu Gln Ser Leu Val Ala Arg Gly Val
            20                  25                  30
```

```
Gly Gly Ser Leu Gly Gly Gly Ala Gly Asp Asp Ala Glu Pro Leu Ser
        35                  40                  45

<210> SEQ ID NO 25
<211> LENGTH: 21
<212> TYPE: PRT
<213> ORGANISM: Homo sapiens

<400> SEQUENCE: 25

Asp Asp Pro Pro Leu Ser Ile Asp Leu Thr Phe His Leu Leu Arg Thr
1               5                   10                  15

Leu Leu Glu Ile Glu
            20

<210> SEQ ID NO 26
<211> LENGTH: 8
<212> TYPE: PRT
<213> ORGANISM: Homo sapiens

<400> SEQUENCE: 26

Asn Arg Lys Leu Leu Asp Glu Val
1               5

<210> SEQ ID NO 27
<211> LENGTH: 12
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Side chain-side peptide bond
<220> FEATURE:
<221> NAME/KEY: MOD_RES
<222> LOCATION: (9)..(9)
<223> OTHER INFORMATION: Any amino acid, preferably cyclohexylalanine

<400> SEQUENCE: 27

Glu Ala Glu Lys Asn Arg Lys Leu Xaa Asp Ile Ile
1               5                   10

<210> SEQ ID NO 28
<211> LENGTH: 28
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: D-Trp

<400> SEQUENCE: 28

Leu Leu His Asp Leu Trp Lys Ser Ile Gln Asp Leu Arg Arg Arg Phe
1               5                   10                  15

Phe Leu His His Leu Ile Ala Glu Ile His Thr Ala
            20                  25

<210> SEQ ID NO 29
<211> LENGTH: 32
<212> TYPE: PRT
<213> ORGANISM: Homo sapiens

<400> SEQUENCE: 29

Ile Gln Leu Leu His Asp Lys Gly Lys Ser Ile Gln Asp Leu Arg Arg
1               5                   10                  15

Arg Phe Trp Leu His His Leu Ile Ala Glu Ile His Thr Ala Glu Tyr
            20                  25                  30
```

```
<210> SEQ ID NO 30
<211> LENGTH: 13
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Cyclohexylalanine

<400> SEQUENCE: 30

Gln Glu Ala Glu Lys Asn Arg Lys Leu Ala Asp Ile Ile
1               5                   10
```